US012765945B2

(12) United States Patent
Pham et al.

(10) Patent No.: US 12,765,945 B2
(45) Date of Patent: Oct. 20, 2026

(54) MEDICAL DEVICE WITH AN IRRIGATION MANIFOLD

(71) Applicant: Biosense Webster (Israel) Ltd., Yokneam (IL)

(72) Inventors: Cuong Pham, Westminster, CA (US); Helee Mukul Joshi, Mission Viejo, CA (US); Thanh Nguyen, El Monte, CA (US); Keshava Datta, Chino Hills, CA (US); Arlene Zavala, Corona, CA (US); Anand Rao, Irvine, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 516 days.

(21) Appl. No.: 18/473,148

(22) Filed: Sep. 22, 2023

(65) Prior Publication Data

US 2025/0099167 A1 Mar. 27, 2025

(51) Int. Cl.
*A61B 18/14* (2006.01)
*A61B 18/00* (2006.01)

(52) U.S. Cl.
CPC *A61B 18/1492* (2013.01); *A61B 2018/00029* (2013.01); *A61B 2018/00267* (2013.01); *A61B 2018/00577* (2013.01); *A61B 2218/002* (2013.01)

(58) Field of Classification Search
CPC ...... A61B 18/1492; A61B 2018/00029; A61B 2018/00267; A61B 2018/00577; A61B 2218/002
See application file for complete search history.

(56) References Cited

U.S. PATENT DOCUMENTS 4,699,147 A 10/1987 Chilson et al.
4,940,064 A 7/1990 Desai
5,215,103 A 6/1993 Desai
5,255,679 A 10/1993 Imran
5,293,869 A 3/1994 Edwards et al.
5,309,910 A 5/1994 Edwards et al.
5,313,943 A 5/1994 Houser et al.
5,324,284 A 6/1994 Imran
5,345,936 A 9/1994 Pomeranz et al.
5,365,926 A 11/1994 Desai
5,391,199 A 2/1995 Ben-Haim
5,396,887 A 3/1995 Imran
(Continued)

FOREIGN PATENT DOCUMENTS

CN 111248993 A 6/2020
CN 111248996 A 6/2020
(Continued)

OTHER PUBLICATIONS

Extended European Search Report and Opinion dated Jan. 24, 2025, from corresponding European application No. 24201716.8.

*Primary Examiner* — Michael F Peffley
*Assistant Examiner* — Bo Ouyang

(57) ABSTRACT

The disclosed technology includes irrigation manifold that routes irrigation fluid to an end effector for a medical device. The irrigation manifold includes a housing and a diverter that extend along a longitudinal axis and respectively connect with irrigation tubes. The end effector includes jackets that each define an irrigation conduit connecting with the irrigation manifold to allow an even distribution of irrigation fluid flow through the jackets.

16 Claims, 10 Drawing Sheets

(56) References Cited

U.S. PATENT DOCUMENTS

| | | | |
|---|---|---|---|
| 5,400,783 | A | 3/1995 | Pomeranz et al. |
| 5,411,025 | A | 5/1995 | Webster, Jr. |
| 5,415,166 | A | 5/1995 | Imran |
| 5,443,489 | A | 8/1995 | Ben-Haim |
| 5,456,254 | A | 10/1995 | Pietroski et al. |
| 5,465,717 | A | 11/1995 | Imran et al. |
| 5,476,495 | A | 12/1995 | Kordis et al. |
| 5,499,981 | A | 3/1996 | Kordis |
| 5,526,810 | A | 6/1996 | Wang |
| 5,546,940 | A | 8/1996 | Panescu et al. |
| 5,549,108 | A | 8/1996 | Edwards et al. |
| 5,558,073 | A | 9/1996 | Pomeranz et al. |
| 5,558,091 | A | 9/1996 | Acker et al. |
| 5,577,509 | A | 11/1996 | Panescu et al. |
| 5,595,183 | A | 1/1997 | Swanson et al. |
| 5,598,848 | A | 2/1997 | Swanson et al. |
| 5,609,157 | A | 3/1997 | Panescu et al. |
| 5,628,313 | A | 5/1997 | Webster, Jr. |
| 5,681,280 | A | 10/1997 | Rusk et al. |
| 5,722,401 | A | 3/1998 | Pietroski et al. |
| 5,722,403 | A | 3/1998 | McGee et al. |
| 5,725,525 | A | 3/1998 | Kordis |
| 5,730,128 | A | 3/1998 | Pomeranz et al. |
| 5,772,590 | A | 6/1998 | Webster, Jr. |
| 5,782,899 | A | 7/1998 | Imran |
| 5,823,189 | A | 10/1998 | Kordis |
| 5,881,727 | A | 3/1999 | Edwards |
| 5,893,847 | A | 4/1999 | Kordis |
| 5,904,680 | A | 5/1999 | Kordis et al. |
| 5,911,739 | A | 6/1999 | Kordis et al. |
| 5,928,228 | A | 7/1999 | Kordis et al. |
| 5,968,040 | A | 10/1999 | Swanson et al. |
| 6,014,579 | A | 1/2000 | Pomeranz et al. |
| 6,014,590 | A | 1/2000 | Whayne et al. |
| 6,119,030 | A | 9/2000 | Morency |
| 6,142,993 | A | 11/2000 | Whayne et al. |
| 6,172,499 | B1 | 1/2001 | Ashe |
| 6,216,043 | B1 | 4/2001 | Swanson et al. |
| 6,216,044 | B1 | 4/2001 | Kordis |
| 6,239,724 | B1 | 5/2001 | Doron et al. |
| 6,332,089 | B1 | 12/2001 | Acker et al. |
| 6,428,537 | B1 | 8/2002 | Swanson et al. |
| 6,456,864 | B1 | 9/2002 | Swanson et al. |
| 6,484,118 | B1 | 11/2002 | Govari |
| 6,574,492 | B1 | 6/2003 | Ben-Haim et al. |
| 6,584,345 | B2 | 6/2003 | Govari |
| 6,600,948 | B2 | 7/2003 | Ben-Haim et al. |
| 6,618,612 | B1 | 9/2003 | Acker et al. |
| 6,690,963 | B2 | 2/2004 | Ben-Haim et al. |
| 6,738,655 | B1 | 5/2004 | Sen et al. |
| 6,741,878 | B2 | 5/2004 | Fuimaono et al. |
| 6,748,255 | B2 | 6/2004 | Fuimaono et al. |
| 6,780,183 | B2 | 8/2004 | Jimenez, Jr. et al. |
| 6,788,967 | B2 | 9/2004 | Ben-Haim et al. |
| 6,837,886 | B2 | 1/2005 | Collins et al. |
| 6,866,662 | B2 | 3/2005 | Fuimaono et al. |
| 6,892,091 | B1 | 5/2005 | Ben-Haim et al. |
| 6,970,730 | B2 | 11/2005 | Fuimaono et al. |
| 6,973,340 | B2 | 12/2005 | Fuimaono et al. |
| 6,980,858 | B2 | 12/2005 | Fuimaono et al. |
| 7,048,734 | B1 | 5/2006 | Fleischman et al. |
| 7,149,563 | B2 | 12/2006 | Fuimaono et al. |
| 7,255,695 | B2 | 8/2007 | Falwell et al. |
| 7,257,434 | B2 | 8/2007 | Fuimaono et al. |
| 7,399,299 | B2 | 7/2008 | Daniel et al. |
| 7,410,486 | B2 | 8/2008 | Fuimaono et al. |
| 7,522,950 | B2 | 4/2009 | Fuimaono et al. |
| 7,536,218 | B2 | 5/2009 | Govari et al. |
| RE41,334 | E | 5/2010 | Beatty et al. |
| 7,756,576 | B2 | 7/2010 | Levin |
| 7,846,157 | B2 | 12/2010 | Kozel |
| 7,848,787 | B2 | 12/2010 | Osadchy |
| 7,869,865 | B2 | 1/2011 | Govari et al. |
| 7,930,018 | B2 | 4/2011 | Harlev et al. |
| 8,007,495 | B2 | 8/2011 | McDaniel et al. |
| 8,048,063 | B2 | 11/2011 | Aeby et al. |
| 8,103,327 | B2 | 1/2012 | Harlev et al. |
| 8,167,845 | B2 | 5/2012 | Wang et al. |
| 8,224,416 | B2 | 7/2012 | De La Rama et al. |
| 8,235,988 | B2 | 8/2012 | Davis et al. |
| 8,346,339 | B2 | 1/2013 | Kordis et al. |
| 8,435,232 | B2 | 5/2013 | Aeby et al. |
| 8,447,377 | B2 | 5/2013 | Harlev et al. |
| 8,456,182 | B2 | 6/2013 | Bar-Tal et al. |
| 8,498,686 | B2 | 7/2013 | Grunewald |
| 8,517,999 | B2 | 8/2013 | Pappone et al. |
| 8,545,490 | B2 | 10/2013 | Mihajlovic et al. |
| 8,560,086 | B2 | 10/2013 | Just et al. |
| 8,567,265 | B2 | 10/2013 | Aeby et al. |
| 8,712,550 | B2 | 4/2014 | Grunewald |
| 8,755,861 | B2 | 6/2014 | Harlev et al. |
| 8,825,130 | B2 | 9/2014 | Just et al. |
| 8,906,011 | B2 | 12/2014 | Gelbart et al. |
| 8,945,120 | B2 | 2/2015 | McDaniel et al. |
| 8,979,839 | B2 | 3/2015 | De La Rama et al. |
| 9,037,264 | B2 | 5/2015 | Just et al. |
| 9,131,980 | B2 | 9/2015 | Bloom |
| 9,204,929 | B2 | 12/2015 | Solis |
| 9,277,960 | B2 | 3/2016 | Weinkam et al. |
| 9,314,208 | B1 | 4/2016 | Altmann et al. |
| 9,339,331 | B2 | 5/2016 | Tegg et al. |
| 9,486,282 | B2 | 11/2016 | Solis |
| 9,554,718 | B2 | 1/2017 | Bar-Tal et al. |
| D782,686 | S | 3/2017 | Werneth et al. |
| 9,585,588 | B2 | 3/2017 | Marecki et al. |
| 9,597,036 | B2 | 3/2017 | Aeby et al. |
| 9,687,297 | B2 | 6/2017 | Just et al. |
| 9,693,733 | B2 | 7/2017 | Altmann et al. |
| 9,782,099 | B2 | 10/2017 | Williams et al. |
| 9,788,895 | B2 | 10/2017 | Solis |
| 9,801,681 | B2 | 10/2017 | Laske et al. |
| 9,814,618 | B2 | 11/2017 | Nguyen et al. |
| 9,833,161 | B2 | 12/2017 | Govari |
| 9,894,756 | B2 | 2/2018 | Weinkam et al. |
| 9,895,073 | B2 | 2/2018 | Solis |
| 9,907,609 | B2 | 3/2018 | Cao et al. |
| 9,974,460 | B2 | 5/2018 | Wu et al. |
| 9,986,949 | B2 | 6/2018 | Govari et al. |
| 9,993,160 | B2 | 6/2018 | Salvestro et al. |
| 10,014,607 | B1 | 7/2018 | Govari et al. |
| 10,028,376 | B2 | 7/2018 | Weinkam et al. |
| 10,034,637 | B2 | 7/2018 | Harlev et al. |
| 10,039,494 | B2 | 8/2018 | Altmann et al. |
| 10,045,707 | B2 | 8/2018 | Govari |
| 10,078,713 | B2 | 9/2018 | Auerbach et al. |
| 10,111,623 | B2 | 10/2018 | Jung et al. |
| 10,130,420 | B2 | 11/2018 | Basu et al. |
| 10,136,828 | B2 | 11/2018 | Houben et al. |
| 10,143,394 | B2 | 12/2018 | Solis |
| 10,172,536 | B2 | 1/2019 | Maskara et al. |
| 10,182,762 | B2 | 1/2019 | Just et al. |
| 10,194,818 | B2 | 2/2019 | Williams et al. |
| 10,201,311 | B2 | 2/2019 | Chou et al. |
| 10,219,860 | B2 | 3/2019 | Harlev et al. |
| 10,219,861 | B2 | 3/2019 | Just et al. |
| 10,231,328 | B2 | 3/2019 | Weinkam et al. |
| 10,238,309 | B2 | 3/2019 | Bar-Tal et al. |
| 10,278,590 | B2 | 5/2019 | Salvestro et al. |
| D851,774 | S | 6/2019 | Werneth et al. |
| 10,314,505 | B2 | 6/2019 | Williams et al. |
| 10,314,507 | B2 | 6/2019 | Govari et al. |
| 10,314,648 | B2 | 6/2019 | Ge et al. |
| 10,314,649 | B2 | 6/2019 | Bakos et al. |
| 10,349,855 | B2 | 7/2019 | Zeidan et al. |
| 10,350,003 | B2 | 7/2019 | Weinkam et al. |
| 10,362,991 | B2 | 7/2019 | Tran et al. |
| 10,375,827 | B2 | 8/2019 | Weinkam et al. |
| 10,376,170 | B2 | 8/2019 | Quinn et al. |
| 10,376,221 | B2 | 8/2019 | Iyun et al. |
| 10,398,348 | B2 | 9/2019 | Osadchy et al. |
| 10,403,053 | B2 | 9/2019 | Katz et al. |
| 10,441,188 | B2 | 10/2019 | Katz et al. |
| 10,470,682 | B2 | 11/2019 | Deno et al. |
| 10,470,714 | B2 | 11/2019 | Altmann et al. |

(56) References Cited

U.S. PATENT DOCUMENTS

| | | | | |
|---|---|---|---|---|
| 10,482,198 | B2 | 11/2019 | Auerbach et al. | |
| 10,492,857 | B2 | 12/2019 | Guggenberger et al. | |
| 10,542,620 | B2 | 1/2020 | Weinkam et al. | |
| 10,575,743 | B2 | 3/2020 | Basu et al. | |
| 10,575,745 | B2 | 3/2020 | Solis | |
| 10,582,871 | B2 | 3/2020 | Williams et al. | |
| 10,582,894 | B2 | 3/2020 | Ben Zrihem et al. | |
| 10,596,346 | B2 | 3/2020 | Aeby et al. | |
| 10,602,947 | B2 | 3/2020 | Govari et al. | |
| 10,617,867 | B2 | 4/2020 | Viswanathan et al. | |
| 10,660,702 | B2 | 5/2020 | Viswanathan et al. | |
| 10,667,753 | B2 | 6/2020 | Werneth et al. | |
| 10,674,929 | B2 | 6/2020 | Houben et al. | |
| 10,681,805 | B2 | 6/2020 | Weinkam et al. | |
| 10,682,181 | B2 | 6/2020 | Cohen et al. | |
| 10,687,892 | B2 | 6/2020 | Long et al. | |
| 10,702,178 | B2 | 7/2020 | Dahlen et al. | |
| 10,716,477 | B2 | 7/2020 | Salvestro et al. | |
| 10,758,304 | B2 | 9/2020 | Aujla | |
| 10,765,371 | B2 | 9/2020 | Hayam et al. | |
| 10,772,566 | B2 | 9/2020 | Aujila | |
| 10,799,281 | B2 | 10/2020 | Goertzen et al. | |
| 10,842,558 | B2 | 11/2020 | Harlev et al. | |
| 10,842,561 | B2 | 11/2020 | Viswanathan et al. | |
| 10,863,914 | B2 | 12/2020 | Govari et al. | |
| 10,881,376 | B2 | 1/2021 | Shemesh et al. | |
| 10,898,139 | B2 | 1/2021 | Guta et al. | |
| 10,905,329 | B2 | 2/2021 | Bar-Tal et al. | |
| 10,912,484 | B2 | 2/2021 | Ziv-Ari et al. | |
| 10,918,306 | B2 | 2/2021 | Govari et al. | |
| 10,939,871 | B2 | 3/2021 | Altmann et al. | |
| 10,952,795 | B2 | 3/2021 | Cohen et al. | |
| 10,973,426 | B2 | 4/2021 | Williams et al. | |
| 10,973,461 | B2 | 4/2021 | Baram et al. | |
| 10,987,045 | B2 | 4/2021 | Basu et al. | |
| 11,006,902 | B1 | 5/2021 | Bonyak et al. | |
| 11,040,208 | B1 | 6/2021 | Govari et al. | |
| 11,045,628 | B2 | 6/2021 | Beeckler et al. | |
| 11,051,877 | B2 | 7/2021 | Sliwa et al. | |
| 11,109,788 | B2 | 9/2021 | Rottmann et al. | |
| 11,116,435 | B2 | 9/2021 | Urman et al. | |
| 11,129,574 | B2 | 9/2021 | Cohen et al. | |
| 11,160,482 | B2 | 11/2021 | Solis | |
| 11,164,371 | B2 | 11/2021 | Yellin et al. | |
| 2002/0198522 | A1 | 12/2002 | Kordis | |
| 2004/0210121 | A1 | 10/2004 | Fuimaono et al. | |
| 2005/0154386 | A1 | 7/2005 | West et al. | |
| 2006/0009689 | A1 | 1/2006 | Fuimaono et al. | |
| 2006/0009690 | A1 | 1/2006 | Fuimaono et al. | |
| 2006/0100669 | A1 | 5/2006 | Fuimaono et al. | |
| 2007/0093806 | A1 | 4/2007 | Desai et al. | |
| 2007/0161966 | A1* | 7/2007 | West | A61B 18/04 606/41 |
| 2007/0276212 | A1 | 11/2007 | Fuimaono et al. | |
| 2008/0234564 | A1 | 9/2008 | Beatty et al. | |
| 2010/0168647 | A1 | 7/2010 | Tegg et al. | |
| 2011/0118726 | A1 | 5/2011 | De La Rama et al. | |
| 2011/0160574 | A1 | 6/2011 | Harlev et al. | |
| 2011/0190625 | A1 | 8/2011 | Harlev et al. | |
| 2011/0245756 | A1 | 10/2011 | Arora et al. | |
| 2011/0301597 | A1 | 12/2011 | McDaniel et al. | |
| 2013/0090651 | A1 | 4/2013 | Smith | |
| 2013/0116688 | A1 | 5/2013 | Kunis et al. | |
| 2013/0172715 | A1 | 7/2013 | Just et al. | |
| 2013/0172872 | A1 | 7/2013 | Subramaniam et al. | |
| 2013/0172883 | A1 | 7/2013 | Lopes et al. | |
| 2013/0178850 | A1 | 7/2013 | Lopes et al. | |
| 2013/0190587 | A1 | 7/2013 | Lopes et al. | |
| 2013/0296852 | A1 | 11/2013 | Madjarov et al. | |
| 2014/0018788 | A1 | 1/2014 | Engelman et al. | |
| 2014/0025069 | A1 | 1/2014 | Willard et al. | |
| 2014/0052118 | A1 | 2/2014 | Laske et al. | |
| 2014/0180147 | A1 | 6/2014 | Thakur et al. | |
| 2014/0180151 | A1 | 6/2014 | Maskara et al. | |
| 2014/0180152 | A1 | 6/2014 | Maskara et al. | |
| 2014/0257069 | A1 | 9/2014 | Eliason et al. | |
| 2014/0276712 | A1 | 9/2014 | Mallin et al. | |
| 2014/0276788 | A1* | 9/2014 | Nguyen | A61B 18/1492 606/41 |
| 2014/0309512 | A1 | 10/2014 | Govari et al. | |
| 2015/0011991 | A1 | 1/2015 | Buysman et al. | |
| 2015/0045863 | A1 | 2/2015 | Litscher et al. | |
| 2015/0080693 | A1 | 3/2015 | Solis | |
| 2015/0105770 | A1 | 4/2015 | Amit | |
| 2015/0119878 | A1 | 4/2015 | Heisel et al. | |
| 2015/0133919 | A1 | 5/2015 | McDaniel et al. | |
| 2015/0208942 | A1 | 7/2015 | Bar-Tal et al. | |
| 2015/0250424 | A1 | 9/2015 | Govari et al. | |
| 2015/0270634 | A1 | 9/2015 | Buesseler et al. | |
| 2015/0342491 | A1 | 12/2015 | Marecki et al. | |
| 2015/0342532 | A1 | 12/2015 | Basu et al. | |
| 2016/0081746 | A1 | 3/2016 | Solis | |
| 2016/0113582 | A1 | 4/2016 | Altmann et al. | |
| 2016/0113709 | A1 | 4/2016 | Maor | |
| 2016/0183877 | A1 | 6/2016 | Williams et al. | |
| 2016/0228023 | A1 | 8/2016 | Govari | |
| 2016/0228062 | A1 | 8/2016 | Altmann et al. | |
| 2016/0278853 | A1 | 9/2016 | Ogle et al. | |
| 2016/0302858 | A1 | 10/2016 | Bencini | |
| 2016/0338770 | A1 | 11/2016 | Bar-Tal et al. | |
| 2017/0027638 | A1 | 2/2017 | Solis | |
| 2017/0065227 | A1 | 3/2017 | Marrs et al. | |
| 2017/0071543 | A1 | 3/2017 | Basu et al. | |
| 2017/0071544 | A1 | 3/2017 | Basu et al. | |
| 2017/0071665 | A1 | 3/2017 | Solis | |
| 2017/0095173 | A1 | 4/2017 | Bar-Tal et al. | |
| 2017/0100187 | A1* | 4/2017 | Basu | A61B 18/1492 |
| 2017/0143227 | A1 | 5/2017 | Marecki et al. | |
| 2017/0156790 | A1 | 6/2017 | Aujla | |
| 2017/0172442 | A1 | 6/2017 | Govari | |
| 2017/0185702 | A1 | 6/2017 | Auerbach et al. | |
| 2017/0202515 | A1 | 7/2017 | Zrihem et al. | |
| 2017/0221262 | A1 | 8/2017 | Laughner et al. | |
| 2017/0224958 | A1 | 8/2017 | Cummings et al. | |
| 2017/0265812 | A1 | 9/2017 | Williams et al. | |
| 2017/0273738 | A1 | 9/2017 | Wu | |
| 2017/0281031 | A1 | 10/2017 | Houben et al. | |
| 2017/0281268 | A1 | 10/2017 | Tran et al. | |
| 2017/0296125 | A1 | 10/2017 | Altmann et al. | |
| 2017/0296251 | A1 | 10/2017 | Wu et al. | |
| 2017/0319269 | A1* | 11/2017 | Oliverius | A61B 18/1492 |
| 2017/0347959 | A1 | 12/2017 | Guta et al. | |
| 2017/0354338 | A1 | 12/2017 | Levin et al. | |
| 2017/0354339 | A1 | 12/2017 | Zeidan et al. | |
| 2017/0354364 | A1 | 12/2017 | Bar-Tal et al. | |
| 2018/0008203 | A1 | 1/2018 | Iyun et al. | |
| 2018/0028084 | A1 | 2/2018 | Williams et al. | |
| 2018/0049803 | A1 | 2/2018 | Solis | |
| 2018/0085064 | A1 | 3/2018 | Auerbach et al. | |
| 2018/0132749 | A1 | 5/2018 | Govari et al. | |
| 2018/0137687 | A1 | 5/2018 | Katz et al. | |
| 2018/0160936 | A1 | 6/2018 | Govari et al. | |
| 2018/0160978 | A1 | 6/2018 | Cohen et al. | |
| 2018/0168511 | A1 | 6/2018 | Hall et al. | |
| 2018/0184982 | A1 | 7/2018 | Basu et al. | |
| 2018/0192958 | A1 | 7/2018 | Wu | |
| 2018/0206792 | A1 | 7/2018 | Auerbach et al. | |
| 2018/0235692 | A1 | 8/2018 | Efimov et al. | |
| 2018/0249959 | A1 | 9/2018 | Osypka | |
| 2018/0256109 | A1 | 9/2018 | Wu et al. | |
| 2018/0279954 | A1 | 10/2018 | Hayam et al. | |
| 2018/0303414 | A1 | 10/2018 | Toth et al. | |
| 2018/0310987 | A1 | 11/2018 | Altmann et al. | |
| 2018/0311497 | A1 | 11/2018 | Mswanathan et al. | |
| 2018/0338722 | A1 | 11/2018 | Altmann et al. | |
| 2018/0344188 | A1 | 12/2018 | Govari | |
| 2018/0344202 | A1 | 12/2018 | Bar-Tal et al. | |
| 2018/0344251 | A1 | 12/2018 | Harlev et al. | |
| 2018/0344393 | A1 | 12/2018 | Gruba et al. | |
| 2018/0360534 | A1 | 12/2018 | Teplitsky et al. | |
| 2018/0365355 | A1 | 12/2018 | Auerbach et al. | |
| 2019/0000540 | A1 | 1/2019 | Cohen et al. | |
| 2019/0008582 | A1 | 1/2019 | Govari et al. | |
| 2019/0015007 | A1 | 1/2019 | Rottmann et al. | |

(56) References Cited

U.S. PATENT DOCUMENTS

| | | | |
|---|---|---|---|
| 2019/0030328 | A1 | 1/2019 | Stewart et al. |
| 2019/0049433 | A1 | 2/2019 | Ehret et al. |
| 2019/0053708 | A1 | 2/2019 | Gliner |
| 2019/0059766 | A1 | 2/2019 | Houben et al. |
| 2019/0069949 | A1 | 3/2019 | Vrba et al. |
| 2019/0069950 | A1 | 3/2019 | Viswanathan et al. |
| 2019/0069954 | A1 | 3/2019 | Cohen et al. |
| 2019/0117111 | A1 | 4/2019 | Osadchy et al. |
| 2019/0117303 | A1 | 4/2019 | Claude et al. |
| 2019/0117315 | A1 | 4/2019 | Keyes et al. |
| 2019/0125439 | A1 | 5/2019 | Rohl et al. |
| 2019/0133552 | A1 | 5/2019 | Shemesh et al. |
| 2019/0142293 | A1 | 5/2019 | Solis |
| 2019/0164633 | A1 | 5/2019 | Ingel et al. |
| 2019/0167137 | A1 | 6/2019 | Bar-Tal et al. |
| 2019/0167140 | A1 | 6/2019 | Williams et al. |
| 2019/0188909 | A1 | 6/2019 | Yellin et al. |
| 2019/0201664 | A1 | 7/2019 | Govari |
| 2019/0209089 | A1 | 7/2019 | Baram et al. |
| 2019/0216346 | A1 | 7/2019 | Ghodrati et al. |
| 2019/0216347 | A1 | 7/2019 | Ghodrati et al. |
| 2019/0231421 | A1 | 8/2019 | Viswanathan et al. |
| 2019/0231423 | A1 | 8/2019 | Weinkam et al. |
| 2019/0239811 | A1 | 8/2019 | Just et al. |
| 2019/0246935 | A1 | 8/2019 | Govari et al. |
| 2019/0298442 | A1 | 10/2019 | Ogata et al. |
| 2019/0314083 | A1 | 10/2019 | Herrera et al. |
| 2019/0328260 | A1 | 10/2019 | Zeidan et al. |
| 2019/0343580 | A1 | 11/2019 | Nguyen et al. |
| 2020/0000518 | A1 | 1/2020 | Kiernan et al. |
| 2020/0008705 | A1 | 1/2020 | Ziv-Ari et al. |
| 2020/0008869 | A1 | 1/2020 | Byrd |
| 2020/0009378 | A1 | 1/2020 | Stewart et al. |
| 2020/0015890 | A1 | 1/2020 | To et al. |
| 2020/0022653 | A1 | 1/2020 | Moisa |
| 2020/0029845 | A1 | 1/2020 | Baram et al. |
| 2020/0046421 | A1 | 2/2020 | Govari |
| 2020/0046423 | A1 | 2/2020 | Viswanathan et al. |
| 2020/0060569 | A1 | 2/2020 | Tegg |
| 2020/0077959 | A1 | 3/2020 | Altmann et al. |
| 2020/0093539 | A1 | 3/2020 | Long et al. |
| 2020/0129089 | A1 | 4/2020 | Gliner et al. |
| 2020/0129125 | A1 | 4/2020 | Govari et al. |
| 2020/0129128 | A1 | 4/2020 | Gliner et al. |
| 2020/0155194 | A1 | 5/2020 | Schneider et al. |
| 2020/0163707 | A1 | 5/2020 | Sliwa et al. |
| 2020/0179650 | A1 | 6/2020 | Beeckler et al. |
| 2020/0196896 | A1 | 6/2020 | Solis |
| 2020/0205689 | A1 | 7/2020 | Squires et al. |
| 2020/0205690 | A1 | 7/2020 | Williams et al. |
| 2020/0205737 | A1 | 7/2020 | Beeckler |
| 2020/0205876 | A1 | 7/2020 | Govari |
| 2020/0205892 | A1 | 7/2020 | Viswanathan et al. |
| 2020/0206461 | A1 | 7/2020 | Govari et al. |
| 2020/0206498 | A1 | 7/2020 | Arora et al. |
| 2020/0289197 | A1 | 9/2020 | Viswanathan et al. |
| 2020/0297234 | A1 | 9/2020 | Houben et al. |
| 2020/0297281 | A1 | 9/2020 | Basu et al. |
| 2020/0305726 | A1 | 10/2020 | Salvestro et al. |
| 2020/0305946 | A1 | 10/2020 | DeSimone et al. |
| 2020/0375657 | A1 | 12/2020 | Olson et al. |
| 2020/0397328 | A1 | 12/2020 | Altmann et al. |
| 2020/0398048 | A1 | 12/2020 | Krimsky et al. |
| 2021/0015549 | A1 | 1/2021 | Haghighi-Mood et al. |
| 2021/0022684 | A1 | 1/2021 | Govari et al. |
| 2021/0045805 | A1 | 2/2021 | Govari et al. |
| 2021/0059549 | A1 | 3/2021 | Urman et al. |
| 2021/0059550 | A1 | 3/2021 | Urman et al. |
| 2021/0059608 | A1 | 3/2021 | Beeckler et al. |
| 2021/0059743 | A1 | 3/2021 | Govari |
| 2021/0059747 | A1 | 3/2021 | Krans et al. |
| 2021/0077184 | A1 | 3/2021 | Basu et al. |
| 2021/0082157 | A1 | 3/2021 | Rosenberg et al. |
| 2021/0085200 | A1 | 3/2021 | Auerbach et al. |
| 2021/0085204 | A1 | 3/2021 | Auerbach et al. |
| 2021/0085215 | A1 | 3/2021 | Auerbach et al. |
| 2021/0085387 | A1 | 3/2021 | Amit et al. |
| 2021/0093292 | A1 | 4/2021 | Baram et al. |
| 2021/0093294 | A1 | 4/2021 | Shemesh et al. |
| 2021/0093374 | A1 | 4/2021 | Govari et al. |
| 2021/0093377 | A1 | 4/2021 | Herrera et al. |
| 2021/0100612 | A1 | 4/2021 | Baron et al. |
| 2021/0113822 | A1 | 4/2021 | Beeckler et al. |
| 2021/0127999 | A1 | 5/2021 | Govari et al. |
| 2021/0128010 | A1 | 5/2021 | Govari et al. |
| 2021/0133516 | A1 | 5/2021 | Govari et al. |
| 2021/0145282 | A1 | 5/2021 | Bar-Tal et al. |
| 2021/0161592 | A1 | 6/2021 | Altmann et al. |
| 2021/0162210 | A1 | 6/2021 | Altmann et al. |
| 2021/0169421 | A1 | 6/2021 | Govari |
| 2021/0169550 | A1 | 6/2021 | Govari et al. |
| 2021/0169567 | A1 | 6/2021 | Govari et al. |
| 2021/0169568 | A1 | 6/2021 | Govari et al. |
| 2021/0177294 | A1 | 6/2021 | Gliner et al. |
| 2021/0177356 | A1 | 6/2021 | Gliner et al. |
| 2021/0177503 | A1 | 6/2021 | Altmann et al. |
| 2021/0178166 | A1 | 6/2021 | Govari et al. |
| 2021/0186363 | A1 | 6/2021 | Gliner et al. |
| 2021/0186604 | A1 | 6/2021 | Altmann et al. |
| 2021/0196372 | A1 | 7/2021 | Altmann et al. |
| 2021/0196394 | A1 | 7/2021 | Govari et al. |
| 2021/0212591 | A1 | 7/2021 | Govari et al. |
| 2021/0219904 | A1 | 7/2021 | Yarnitsky et al. |
| 2021/0278936 | A1 | 9/2021 | Katz et al. |
| 2021/0282659 | A1 | 9/2021 | Govari et al. |
| 2021/0307815 | A1 | 10/2021 | Govari et al. |
| 2021/0308424 | A1 | 10/2021 | Beeckler et al. |
| 2021/0338319 | A1 | 11/2021 | Govari et al. |
| 2022/0370124 | A1 | 11/2022 | Haghighi-Mood et al. |
| 2023/0012307 | A1 | 1/2023 | Harlev et al. |
| 2023/0225789 | A1 | 7/2023 | Okarski et al. |

FOREIGN PATENT DOCUMENTS

| | | | |
|---|---|---|---|
| DE | 202023102290 | U1 | 8/2023 |
| DE | 202023102282 | U1 | 9/2023 |
| EP | 0668740 | A1 | 8/1995 |
| EP | 0644738 | B1 | 3/2000 |
| EP | 0727183 | B1 | 11/2002 |
| EP | 0727184 | B1 | 12/2002 |
| EP | 2699153 | A1 | 2/2014 |
| EP | 2783651 | A1 | 10/2014 |
| EP | 2699151 | B1 | 11/2015 |
| EP | 2699152 | B1 | 11/2015 |
| EP | 2498706 | B1 | 4/2016 |
| EP | 2578173 | B1 | 6/2017 |
| EP | 3238645 | A1 | 11/2017 |
| EP | 2884931 | B1 | 1/2018 |
| EP | 3241493 | B1 | 2/2019 |
| EP | 2349440 | B1 | 8/2019 |
| EP | 3318211 | B1 | 12/2019 |
| EP | 3581135 | A1 | 12/2019 |
| EP | 2736434 | B1 | 2/2020 |
| EP | 3451962 | B1 | 3/2020 |
| EP | 3972510 | A1 | 3/2022 |
| WO | 9421167 | A1 | 9/1994 |
| WO | 9421169 | A1 | 9/1994 |
| WO | 9625095 | A1 | 8/1996 |
| WO | 9634560 | A1 | 11/1996 |
| WO | 0182814 | A2 | 5/2002 |
| WO | 2004087249 | A2 | 10/2004 |
| WO | 2012100185 | A2 | 7/2012 |
| WO | 2013052852 | A1 | 4/2013 |
| WO | 2013162884 | A1 | 10/2013 |
| WO | 2013173917 | A1 | 11/2013 |
| WO | 2013176881 | A1 | 11/2013 |
| WO | 2014176205 | A1 | 10/2014 |
| WO | 2016019760 | A1 | 2/2016 |
| WO | 2016044687 | A1 | 3/2016 |
| WO | 2017066087 | A1 | 4/2017 |
| WO | 2018111600 | A1 | 6/2018 |
| WO | 2018191149 | A1 | 10/2018 |
| WO | 2019084442 | A1 | 5/2019 |
| WO | 2019143960 | A1 | 7/2019 |

(56) References Cited

FOREIGN PATENT DOCUMENTS

| | | | |
|---|---|---|---|
| WO | 2020026217 | A1 | 2/2020 |
| WO | 2020206328 | A1 | 10/2020 |
| WO | 2021126980 | A1 | 6/2021 |

* cited by examiner

MEDICAL DEVICE WITH AN IRRIGATION MANIFOLD

FIELD

The present technology relates generally to medical devices, and in particular medical probes with electrodes, and further relates to, but not exclusively, medical probes suitable for use to induce irreversible electroporation (IRE) of cardiac tissues.

BACKGROUND

Cardiac arrhythmias, such as atrial fibrillation (AF), occur when regions of cardiac tissue abnormally conduct electric signals to adjacent tissue. This disrupts the normal cardiac cycle and causes asynchronous rhythm. Certain procedures exist for treating arrhythmia, including surgically disrupting the origin of the signals causing the arrhythmia and disrupting the conducting pathway for such signals. By selectively ablating cardiac tissue by application of energy via a catheter, it is sometimes possible to cease or modify the propagation of unwanted electrical signals from one portion of the heart to another.

Many current ablation approaches in the art utilize radiofrequency (RF) electrical energy to heat tissue. RF ablation can have certain risks related to thermal heating which can lead to tissue charring, burning, steam pop, phrenic nerve palsy, pulmonary vein stenosis, and esophageal fistula.

Cryoablation is an alternative approach to RF ablation that generally reduces thermal risks associated with RF ablation. Maneuvering cryoablation devices and selectively applying cryoablation, however, is generally more challenging compared to RF ablation; therefore, cryoablation is not viable in certain anatomical geometries which may be reached by electrical ablation devices.

Some ablation approaches use irreversible electroporation (IRE) to ablate cardiac tissue using nonthermal ablation methods. IRE delivers short pulses of high voltage to tissues and generates an unrecoverable permeabilization of cell membranes. Delivery of IRE energy to tissues using multi-electrode probes was previously proposed in the patent literature. Examples of systems and devices configured for IRE ablation are disclosed in U.S. Patent Pub. No. 2021/0169550A1, 2021/0169567A1, 2021/0169568A1, 2021/0161592A1, 2021/0196372A1, 2021/0177503A1, and 2021/0186604A1, each of which are incorporated herein by reference.

Irrigation, while employing IRE ablation, is required to ensure no thrombosis occurs. However, it is a challenge to ensure even irrigation around the electrodes. Accordingly, there is a need for improved techniques to evenly distribute irrigation fluid flow around each electrode.

SUMMARY

There is provided, in accordance with the disclosed technology, an irrigation manifold for a medical device. The irrigation manifold can include a housing extending along a longitudinal axis defining a housing lumen and a housing conduit offset from the housing lumen, the housing conduit being configured to connect with a main line irrigation tube. The irrigation manifold can include a diverter defining a diverter lumen connecting with the housing to define an irrigation chamber. The diverter can include a first shaft nesting within the housing lumen. The diverter can include a diverter ring defining a plurality of diverter conduits disposed radially about the longitudinal axis and connecting with a distal end of the housing. Each diverter conduit is configured to connect with a diverter irrigation tube that routes a fluid to an end effector of the medical device.

There is further provided, in accordance with the disclosed technology, an end effector for a medical device. The end effector can include an irrigation manifold, at least one spine, and an actuator rod. The irrigation manifold extends along a longitudinal axis and can include a housing and a diverter. The housing defines a housing lumen and a housing conduit. The diverter defines a diverter lumen, connects with the housing to define an irrigation chamber, and defines at least one diverter conduit. Fluid is configured to flow into the irrigation chamber via the housing conduit and out of the irrigation chamber via the at least one diverter conduit. The at least one spine is connected to the irrigation manifold at a proximal end of the at least one spine and is configured to bow radially outward from the longitudinal axis and to move between an expanded configuration and a collapsed configuration. The at least one diverter conduit is configured to route the fluid along the at least one spine. The actuator rod passes through the housing lumen and the diverter lumen and is connected to a distal end of the at least one spine. The actuator rod is configured to move the at least one spine between the expanded configuration and the collapsed configuration.

DETAILED DESCRIPTION

Figure 1:
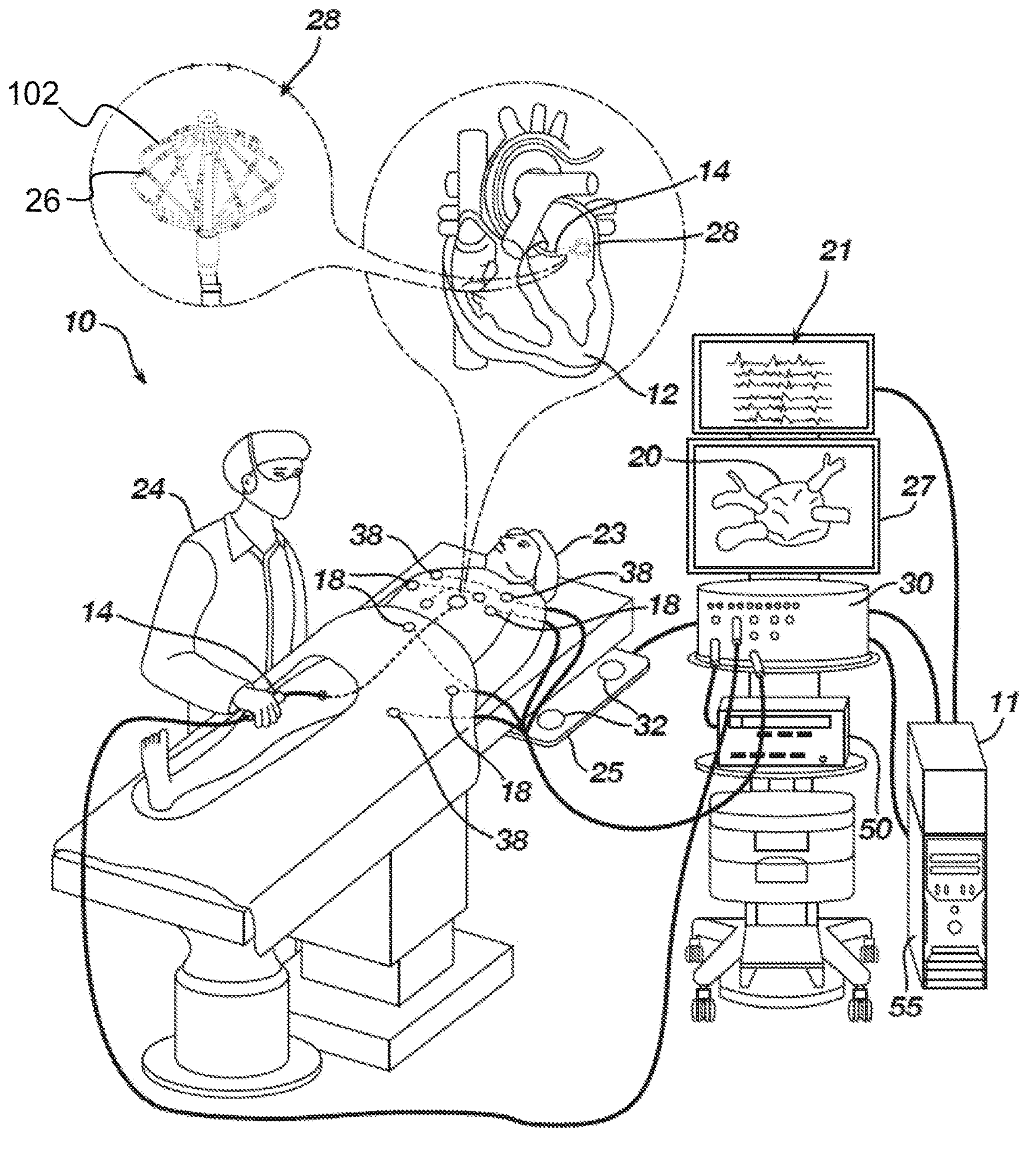
FIG. 1 is a schematic pictorial illustration of a medical system including a medical device with a distal end that includes a medical probe with electrodes, in accordance with the disclosed technology.

The following detailed description should be read with reference to the drawings, in which like elements in different drawings are identically numbered. The drawings, which are not necessarily to scale, depict selected examples and are not intended to limit the scope of the present disclosure. The detailed description illustrates by way of example, not by way of limitation, the principles of the disclosed technology. This description will clearly enable one skilled in the art to make and use the disclosed technology, and describes several embodiments, adaptations, variations, alternatives and uses of the disclosed technology, including what is presently believed to be the best mode of carrying out the disclosed technology.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 110%. In addition, as used herein, the terms "patient," "host," "user," and "subject" refer to any human or animal subject and are not intended to limit the systems or methods to human use, although use of the subject technology in a human patient represents a preferred embodiment. As well, the term "proximal" indicates a location closer to the operator or physician whereas "distal" indicates a location further away to the operator or physician.

As discussed herein, vasculature of a "patient," "host," "user," and "subject" can be vasculature of a human or any animal. It should be appreciated that an animal can be a variety of any applicable type, including, but not limited thereto, mammal, veterinarian animal, livestock animal or pet type animal, etc. As an example, the animal can be a laboratory animal specifically selected to have certain characteristics similar to a human (e.g., rat, dog, pig, monkey, or the like). It should be appreciated that the subject can be any applicable human patient, for example.

As discussed herein, "operator" can include a doctor, surgeon, technician, scientist, or any other individual or delivery instrumentation associated with delivery of a multi-electrode catheter for the treatment of drug refractory atrial fibrillation to a subject.

As discussed herein, the term "ablate" or "ablation", as it relates to the devices and corresponding systems of this disclosure, refers to components and structural features configured to reduce or prevent the generation of erratic cardiac signals in the cells by utilizing non-thermal energy, such as irreversible electroporation (IRE), referred throughout this disclosure interchangeably as pulsed electric field (PEF) and pulsed field ablation (PFA). Ablating or ablation as it relates to the devices and corresponding systems of this disclosure is used throughout this disclosure in reference to non-thermal ablation of cardiac tissue for certain conditions including, but not limited to, arrhythmias, atrial flutter ablation, pulmonary vein isolation, supraventricular tachycardia ablation, and ventricular tachycardia ablation. The term "ablate" or "ablation" also includes known methods, devices, and systems to achieve various forms of bodily tissue ablation as understood by a person skilled in the relevant art.

As discussed herein, the terms "bipolar" and "unipolar" when used to refer to ablation schemes describe ablation schemes which differ with respect to electrical current path and electric field distribution. "Bipolar" refers to ablation scheme utilizing a current path between two electrodes that are both positioned at a treatment site; current density and electric flux density is typically approximately equal at each of the two electrodes. "Unipolar" refers to ablation scheme utilizing a current path between two electrodes where one electrode having a high current density and high electric flux density is positioned at a treatment site, and a second electrode having comparatively lower current density and lower electric flux density is positioned remotely from the treatment site.

As discussed herein, the terms "tubular", "tube" and "shaft" are to be construed broadly and are not limited to a structure that is a right cylinder or strictly circumferential in cross-section or of a uniform cross-section throughout its length. For example, the tubular/shaft structures are generally illustrated as a substantially right cylindrical structure. However, the tubular/shaft structures may have a tapered or curved outer surface without departing from the scope of the present disclosure.

The present disclosure is related to systems, method or uses and devices for IRE ablation of cardiac tissue to treat cardiac arrhythmias. Ablative energies are typically provided to cardiac tissue by a tip portion of a catheter which can deliver ablative energy alongside the tissue to be ablated. Some example catheters include three-dimensional structures at the tip portion and are configured to administer ablative energy from various electrodes positioned on the three-dimensional structures. Ablative procedures incorporating such example catheters can be visualized using fluoroscopy.

Ablation of cardiac tissue using application of a thermal technique, such as radio frequency (RF) energy and cryoablation, to correct a malfunctioning heart is a well-known procedure. Typically, to successfully ablate using a thermal technique, cardiac electropotentials need to be measured at various locations of the myocardium. In addition, temperature measurements during ablation provide data enabling the efficacy of the ablation. Typically, for an ablation procedure using a thermal technique, the electropotentials and the temperatures are measured before, during, and after the actual ablation. RF approaches can have risks that can lead to tissue charring, burning, steam pop, phrenic nerve palsy, pulmonary vein stenosis, and esophageal fistula. Cryoablation is an alternative approach to RF ablation that can reduce some thermal risks associated with RF ablation. However maneuvering cryoablation devices and selectively applying cryoablation is generally more challenging compared to RF ablation; therefore, cryoablation is not viable in certain anatomical geometries which may be reached by electrical ablation devices.

The present disclosure can include electrodes configured for irreversible electroporation (IRE), RF ablation, and/or cryoablation. IRE can be referred to throughout this disclosure interchangeably as pulsed electric field (PEF) ablation and pulsed field ablation (PFA). IRE as discussed in this disclosure is a non-thermal cell death technology that can be used for ablation of atrial arrhythmias. To ablate using IRE/PEF, biphasic voltage pulses are applied to disrupt cellular structures of myocardium. The biphasic pulses are non-sinusoidal and can be tuned to target cells based on electrophysiology of the cells. In contrast, to ablate using RF, a sinusoidal voltage waveform is applied to produce heat at the treatment area, indiscriminately heating all cells in the treatment area. IRE therefore has the capability to spare adjacent heat sensitive structures or tissues which would be of benefit in the reduction of possible complications known with ablation or isolation modalities. Additionally, or alternatively, monophasic pulses can be utilized.

Electroporation can be induced by applying a pulsed electric field across biological cells to cause reversable (temporary) or irreversible (permanent) creation of pores in the cell membrane. The cells have a transmembrane electrostatic potential that is increased above a resting potential upon application of the pulsed electric field. While the transmembrane electrostatic potential remains below a threshold potential, the electroporation is reversable, meaning the pores can close when the applied pulse electric field is removed, and the cells can self-repair and survive. If the transmembrane electrostatic potential increases beyond the threshold potential, the electroporation is irreversible, and the cells become permanently permeable. As a result, the cells die due to a loss of homeostasis and typically die by apoptosis. Generally, cells of differing types have differing threshold potential. For instance, heart cells have a threshold potential of approximately 500 V/cm, whereas for bone it is 3000 V/cm. These differences in threshold potential allow IRE to selectively target tissue based on threshold potential.

The technology of this disclosure includes systems and methods for applying electrical signals from catheter electrodes positioned in the vicinity of myocardial tissue to generate a generate ablative energy to ablate the myocardial tissue. In some examples, the systems and methods can be effective to ablate targeted tissue by inducing irreversible electroporation. In some examples, the systems and methods can be effective to induce reversible electroporation as part of a diagnostic procedure. Reversible electroporation occurs when the electricity applied with the electrodes is below the electric field threshold of the target tissue allowing cells to repair. Reversible electroporation does not kill the cells but allows a physician to see the effect of reversible electroporation on electrical activation signals in the vicinity of the target location. Example systems and methods for reversible electroporation is disclosed in U.S. Patent Publication 2021/0162210, the entirety of which is incorporated herein by reference.

The pulsed electric field, and its effectiveness to induce reversible and/or irreversible electroporation, can be affected by physical parameters of the system and biphasic pulse parameters of the electrical signal. Physical parameters can include electrode contact area, electrode spacing, electrode geometry, etc. Examples presented herein generally include physical parameters adapted to effectively induce reversible and/or irreversible electroporation. Biphasic pulse parameters of the electrical signal can include voltage amplitude, pulse duration, pulse interphase delay, inter-pulse delay, total application time, delivered energy, etc. In some examples, parameters of the electrical signal can be adjusted to induce both reversible and irreversible electroporation given the same physical parameters. Examples of various systems and methods of ablation including IRE are presented in U.S. Patent Publications 2021/0169550A1, 2021/0169567A1, 2021/0169568A1, 2021/0161592A1, 2021/0196372A1, 2021/0177503A1, and 2021/0186604A1, the entireties of each of which are incorporated herein by reference.

Reference is made to FIG. 1 showing an example catheter-based electrophysiology mapping and ablation system 10. System 10 includes multiple catheters, which are percutaneously inserted by physician 24 through the patient's 23 vascular system into a chamber or vascular structure of a heart 12. Typically, a delivery sheath catheter is inserted into the left or right atrium near a desired location in heart 12. Thereafter, a plurality of catheters can be inserted into the delivery sheath catheter so as to arrive at the desired location. The plurality of catheters may include catheters dedicated for sensing Intracardiac Electrogram (IEGM) signals, catheters dedicated for ablating and/or catheters dedicated for both sensing and ablating. An example medical device/probe, e.g., a catheter 14, that is configured for sensing IEGM is illustrated herein. Physician 24 brings a distal tip of catheter 14 (i.e., a basket assembly 28 in this case) into contact with the heart wall for sensing a target site in heart 12. A catheter 14 with a distal basket assembly can be referred to as a basket catheter. For ablation, physician 24 would similarly bring a distal end of an ablation catheter to a target site for ablating.

Catheter 14 is an exemplary catheter that includes one and preferably multiple electrodes 26 optionally distributed over a plurality of spines 104 at basket assembly 28 and configured to sense the IEGM signals. Catheter 14 may additionally include a position sensor embedded in or near basket assembly 28 for tracking position and orientation of basket assembly 28. Optionally and preferably, position sensor is a magnetic based position sensor including three magnetic coils for sensing three-dimensional (3D) position and orientation.

Magnetic based position sensor may be operated together with a location pad 25 including a plurality of magnetic coils 32 configured to generate magnetic fields in a predefined working volume. Real time position of basket assembly 28 of catheter 14 may be tracked based on magnetic fields generated with location pad 25 and sensed by magnetic based position sensor. Details of the magnetic based position sensing technology are described in U.S. Pat. Nos. 5,391,199; 5,443,489; 5,558,091; 6,172,499; 6,239,724; 6,332,089; 6,484,118; 6,618,612; 6,690,963; 6,788,967; 6,892,091, each of which are incorporated herein by reference.

System 10 includes one or more electrode patches 38 positioned for skin contact on patient 23 to establish location reference for location pad 25 as well as impedance-based tracking of electrodes 26. For impedance-based tracking, electrical current is directed toward electrodes 26 and sensed at electrode skin patches 38 so that the location of each electrode can be triangulated via the electrode patches 38. Details of the impedance-based location tracking technology are described in U.S. Pat. Nos. 7,536,218; 7,756,576; 7,848,787; 7,869,865; and 8,456,182, each of which are incorporated herein by reference.

A recorder 11 displays electrograms 21 captured with body surface ECG electrodes 18 and intracardiac electrograms (IEGM) captured with electrodes 26 of catheter 14. Recorder 11 may include pacing capability for pacing the heart rhythm and/or may be electrically connected to a standalone pacer.

System 10 may include an ablation energy generator 50 that is adapted to conduct ablative energy to one or more of electrodes at a distal tip of a catheter configured for ablating. Energy produced by ablation energy generator 50 may include, but is not limited to, radiofrequency (RF) energy or pulsed-field ablation (PFA) energy, including monopolar or bipolar high-voltage DC pulses as may be used to effect irreversible electroporation (IRE), or combinations thereof.

Patient interface unit (PIU) 30 is an interface configured to establish electrical communication between catheters, electrophysiological equipment, power supply and a workstation 55 for controlling operation of system 10. Electrophysiological equipment of system 10 may include for example, multiple catheters, location pad 25, body surface ECG electrodes 18, electrode patches 38, ablation energy generator 50, and recorder 11. Optionally and preferably, PIU 30 additionally includes processing capability for implementing real-time computations of location of the catheters and for performing ECG calculations.

Workstation 55 includes memory, processor unit with memory or storage with appropriate operating software loaded therein, and user interface capability. Workstation 55 may provide multiple functions, optionally including (1) modeling the endocardial anatomy in three-dimensions (3D) and rendering the model or anatomical map 20 for display on a display device 27, (2) displaying on display device 27 activation sequences (or other data) compiled from recorded electrograms 21 in representative visual indicia or imagery superimposed on the rendered anatomical map 20, (3) displaying real-time location and orientation of multiple catheters within the heart chamber, and (5) displaying on display device 27 sites of interest such as places where ablation energy has been applied. One commercial product embodying elements of the system 10 is available as the CARTO™ 3 System, available from Biosense Webster, Inc., 31 Technology Drive, Suite 200, Irvine, CA 92618 USA.

Figure 2:
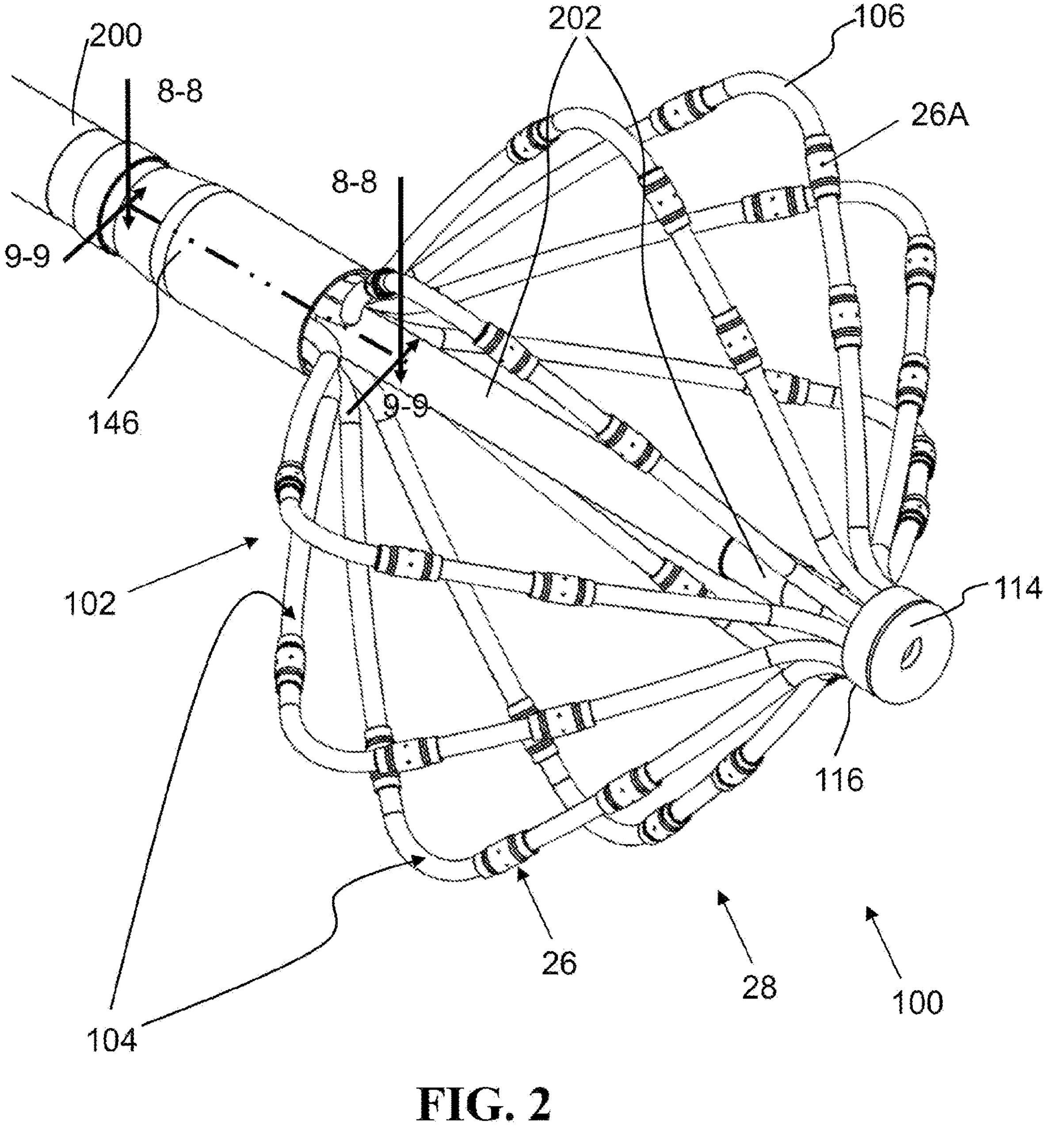
FIG. 2 is a schematic pictorial illustration showing a perspective view of an end effector of the medical device in an expanded configuration, in accordance with the disclosed technology.

FIG. 2 is a schematic pictorial illustration showing a perspective view of a medical device 14, such as a medical probe, with electrodes 26. The medical device 14 includes, at its distal tip 28, an end effector 100. The end effector 100 in the presently described example takes the form of a basket assembly that includes at least one spine 104. Spines 104 may have elliptical (e.g., circular) or rectangular (that may appear to be flat) cross-sections, and include a flexible, resilient material (e.g., a shape-memory alloy such as nickel-titanium, also known as Nitinol) forming a strut.

The end effector 100 is connected to the rest of the medical probe 14 via an elongated shaft 200. The elongated shaft 200 can be tubular in form and flexible, with certain portions being more flexible than others. For example, a tip portion can be made more flexible than the rest to allow the end effector 100 to be easily deflected. The elongated shaft 200 can be formed from a flexible, biocompatible electrically insulative material such as polyamide-polyether (Pebax) copolymers, polyethylene terephthalate (PET), urethanes, polyimide, parylene, silicone, etc. In some examples, insulative material can include biocompatible polymers including, without limitation, polyetheretherketone (PEEK), polyglycolic acid (PGA), poly(lactic-co-glycolic acid) copolymer (PLGA), polycaprolactive (PCL), poly(3-hydroxybutyrate-co-3-hydroxyvalerate) (PHBV), poly-L-lactide, polydioxanone, polycarbonates, and polyanhydrides with the ratio of certain polymers being selected to control the degree of inflammatory response.

Figure 3:
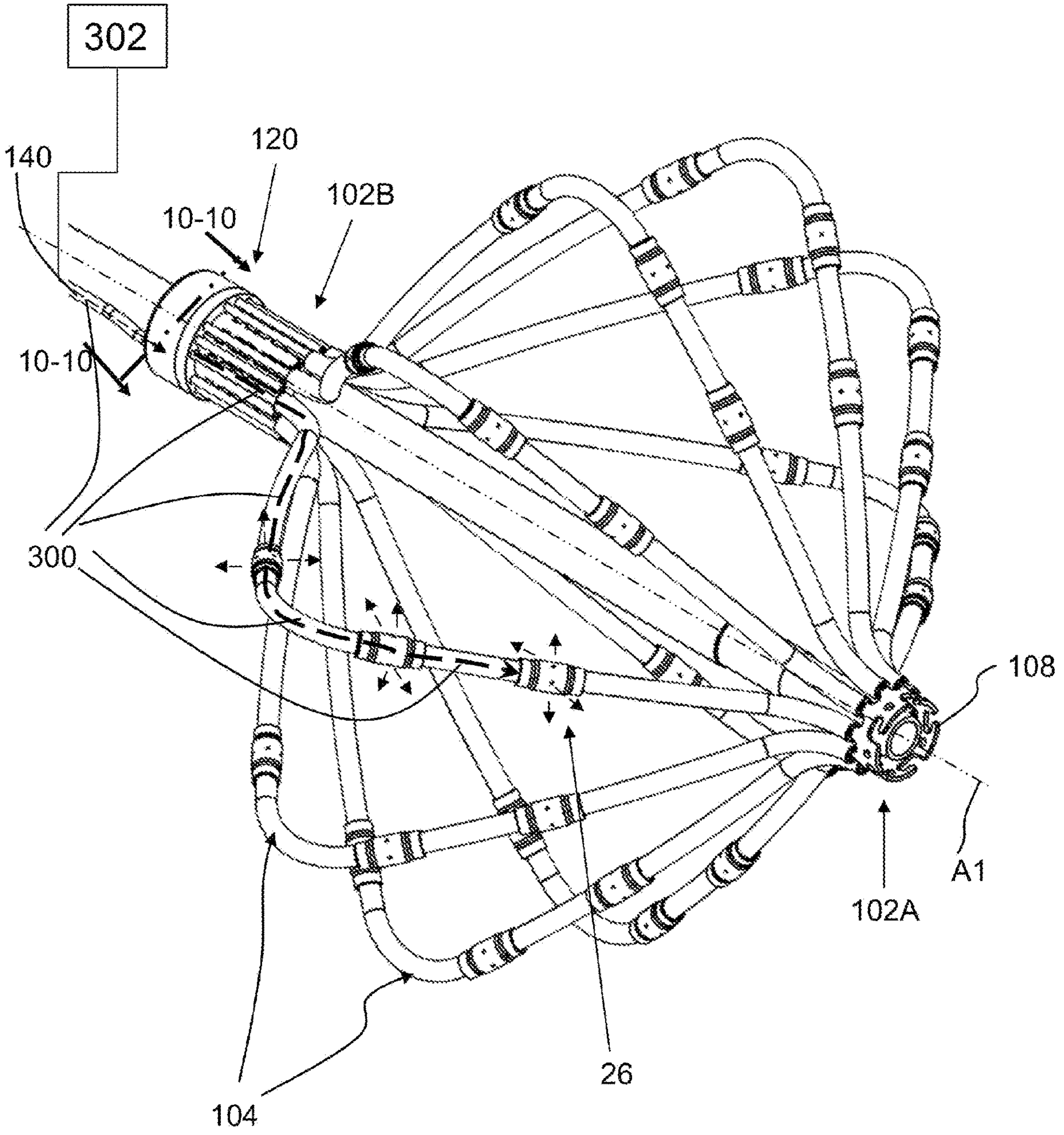
FIG. 3 is a schematic pictorial illustration showing a perspective view of the end effector 100, with the sleeve, coil, and annulus removed for clarity. in accordance with the disclosed technology.

In some examples, the spines 104 may be formed integrally with a distal hub (referred to herein as crown 108), as seen in FIG. 3, so as to form a unitary/monolithic spine framework 102. In other examples, the framework 102 can be formed from a plurality of spines 104 and crown 108 separately formed and connected together. The framework 104 can be formed from a planar or cylindrical tube stock of material using any suitable method. For example, the framework 102 can be formed by cutting, laser cutting, stamping, etc.

An atraumatic annulus 114 and coil 116 are connected to the crown 108. In some examples, the coil 116 can comprise a single axis sensor (SAS). In other examples, the coil 116 can comprise a dual axis sensor (DAS) or a triple axis sensor (TAS). The coil 116 can comprise a conductive material wound in a coil or a coil formed into a flexible circuit. The coil 116 can comprise electrical leads for conduction of current induced on the coil to the patient interface unit 30. As will be appreciated, by attaching a coil 116 to the distal end of the end effector 100, it is possible to detect a position thereof. In this way, a physician 24 can more accurately determine the position of the distal end of the end effector 100 before applying ablative energy to tissue.

An insulative material, referred to herein as a jacket 106, is provided over each spine. Each jacket 106 serves to enhance the atraumaticity of the end effector 100 to protect the subject from sharp edges and for irrigation purposes described in greater detail below. The jacket 106 can include a polymer. For example, the jacket 106 can be formed from a flexible, biocompatible electrically insulative material such as polyamide-polyether (Pebax) copolymers, polyethylene terephthalate (PET), urethanes, polyimide, parylene, silicone, etc. In some examples, insulative material can include biocompatible polymers including, without limitation, polyetheretherketone (PEEK), polyglycolic acid (PGA), poly(lactic-co-glycolic acid) copolymer (PLGA), polycaprolactive (PCL), poly(3-hydroxybutyrate-co-3-hydroxyvalerate) (PHBV), poly-L-lactide, polydioxanone, polycarbonates, and polyanhydrides with the ratio of certain polymers being selected to control the degree of inflammatory response. Furthermore, while the jacket 106 is shown to be tubular in these figures, the jacket 106 can be shaped, scalloped, ribbed, ridged, concaved, convexed, or otherwise configured such that the overall profile of jacket 106 yields physical and/or mechanical properties, such as rigidity and flexion along multiple axes, required by the end effector 100, mentioned above. Moreover, a flexible sleeve 146 is provided over proximal end of the end effector 100 and an irrigation manifold 120 (FIG. 3), which is discussed in greater detail below.

The spine(s) 104 are movable between an expanded configuration and a collapsed configuration. The elongated shaft 200 connects the end effector 100 to a handle that, in use, the operator 24 can manipulate. An actuator rod 202 is connected to the crown 108 to facilitate the expanding and collapsing of the spines 104. For example, the rod 202 can be translated along a longitudinal axis A1 to expand/collapse the spines 104. In the expanded configuration (FIG. 2) as well as the collapsed configuration, one or more spines 104 can bow radially outwardly from the longitudinal axis A1. The spine(s) 104, elongated shaft 200, and actuator rod 202 are arranged generally along the longitudinal axis A1 when the elongated shaft 200 is unbent.

FIG. 3 is a schematic pictorial illustration showing a perspective view of the end effector 100, the sleeve 146, coil 116, and annulus 114 removed for clarity. As shown, the framework 102 has a distal end 102A (that includes the crown 108) and a proximal end 102B. The proximal end 102B is connected with an irrigation manifold 120 that routes irrigation flow 300 therethrough via a fluid source 302 coupled to a main line irrigation tube 140, and is described in greater detail below.

Figure 4:
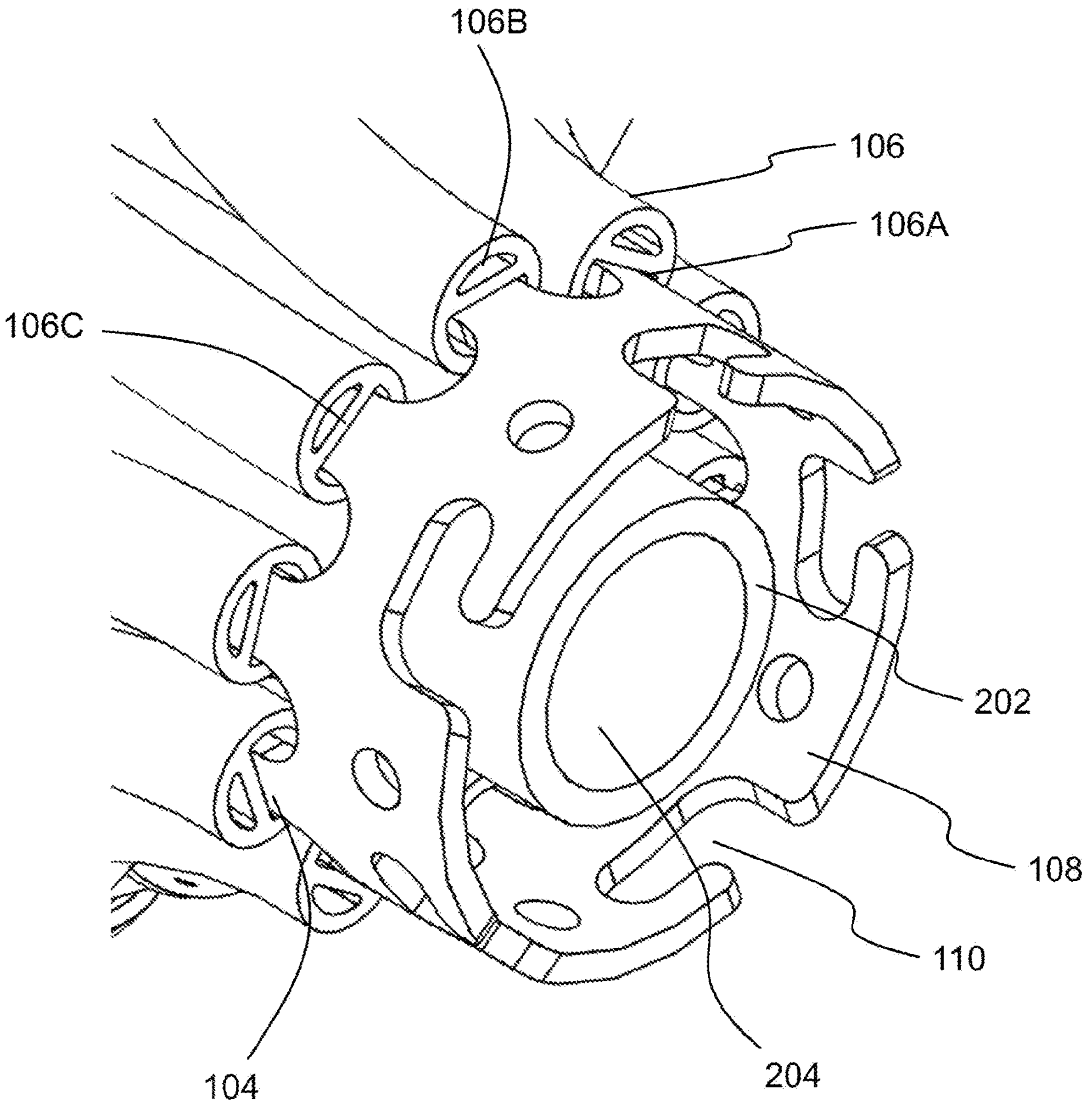
FIG. 4 is a schematic pictorial illustration showing a detail perspective view of a spine framework distal end, in accordance with the disclosed technology.

FIG. 4 is a schematic pictorial illustration showing a detail perspective view of the framework distal end 102A. As shown, the actuator rod 202 extends within a lumen in the crown 108, and the annulus 114 connects the actuator rod 202 to the crown 108 via locking cutouts 110 defined in the crown 108. The actuator rod 202 also defines a lumen 204, which is coaxial with the longitudinal axis A1, through which various medical devices can be extended therethrough when in use, such as a mapping catheter or a guidewire.

Figure 5:
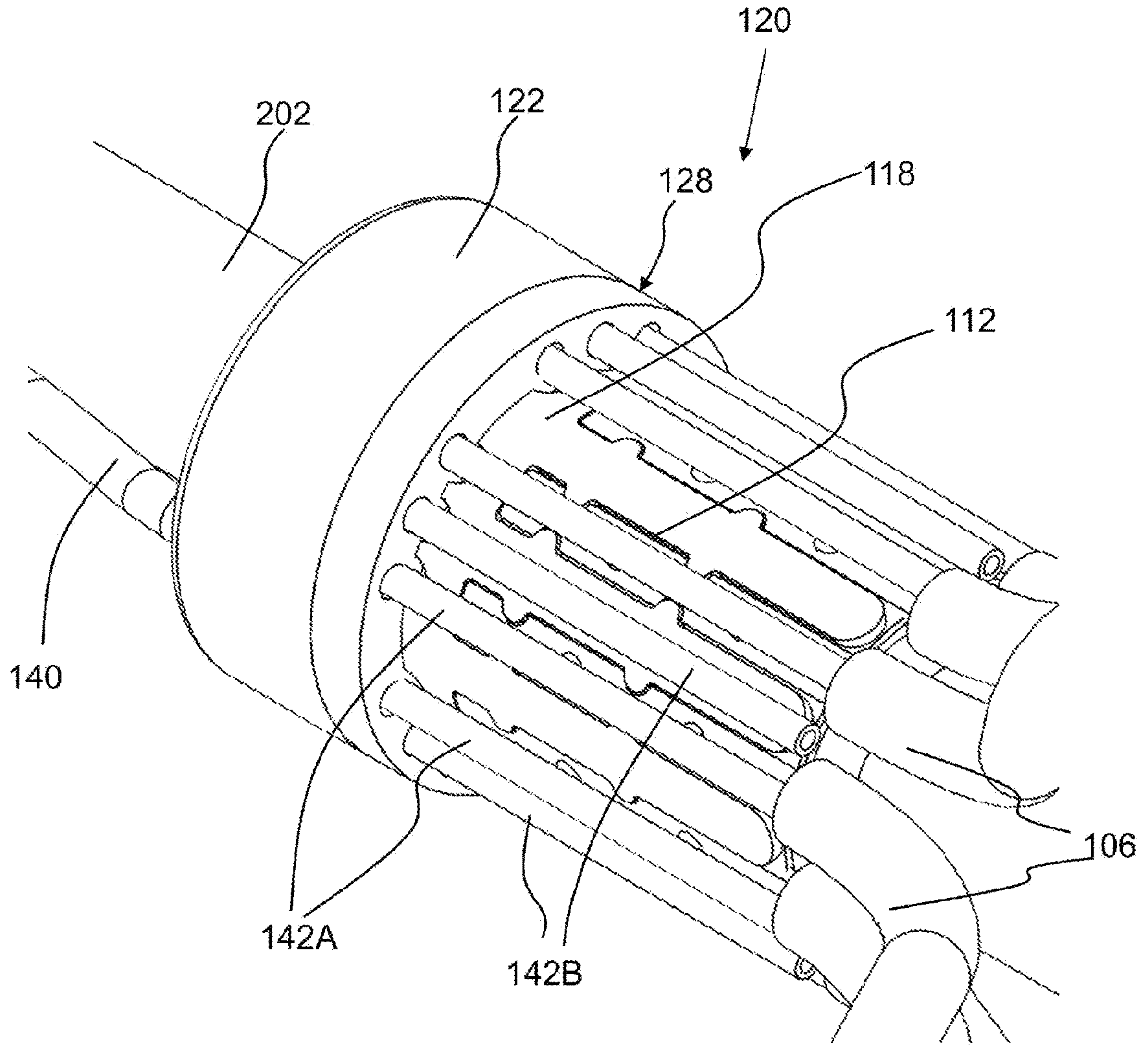
FIG. 5 is a schematic pictorial illustration showing a detail perspective view of a proximal end of the end effector with the sleeve removed, in accordance with the disclosed technology.

With continued reference to FIG. 4, a pair of openings can be seen in the jackets 106 that extend the length thereof. Specifically, each jacket 106 defines a spine channel 106A and an irrigation conduit 106B that are separated by a jacket wall 106C. Each spine channel 106A and irrigation conduit 106B can span an entire length of the jacket 106. The spines 104 extend through the spine channel 106A from the crown 108 and terminate, after exiting the spine channel 106A, at a spine proximal end 112 (FIG. 5). The irrigation conduit 106B routes fluid along the spine 104 and is described in greater detail below.

Figure 6:
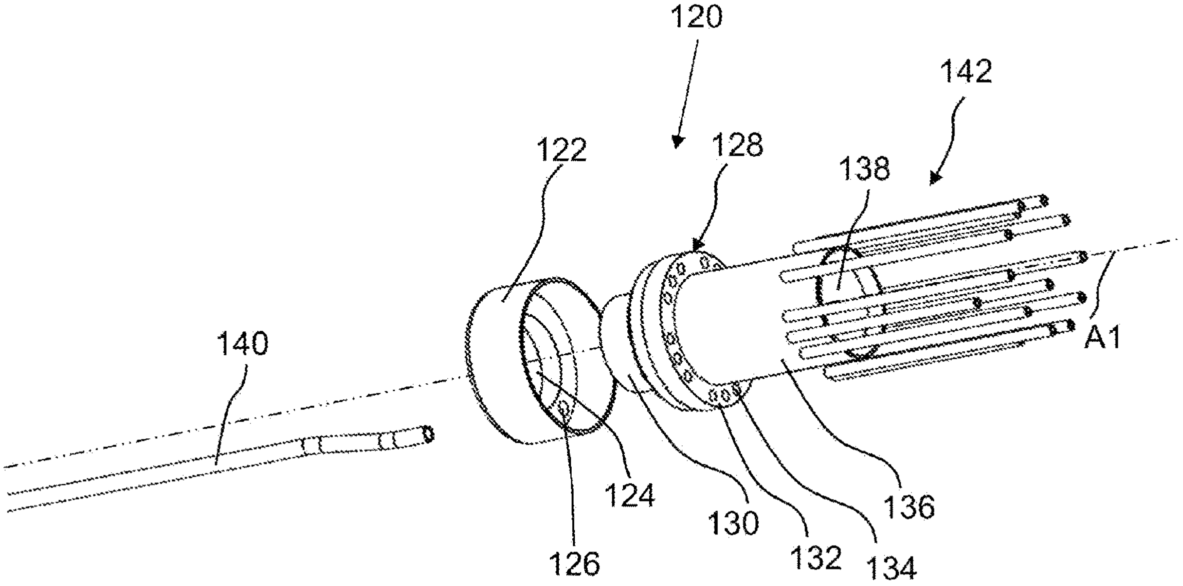
FIG. 6 is a schematic pictorial illustration of an exploded view of an irrigation manifold, a main line irrigation tube, and diverter irrigation tubes, in accordance with the disclosed technology.

FIG. 5 is a schematic pictorial illustration showing a detail perspective view of a proximal end of the end effector 100. FIG. 6 is a schematic pictorial illustration of an exploded view of an irrigation manifold 120, a main line irrigation tube 140, and diverter irrigation tubes 142. Further to the above, and making reference to FIGS. 5 and 6, the distal ends 112 of the spines 104 are connected to a spine coupler 118 that is shaped to conform to the shape of the distal ends 112. The spine coupler 118 is connected to an irrigation manifold 120 that is designed to evenly distribute irrigation fluid 300 in a region the end effector 100 is positioned within a patient 23. The irrigation manifold 120 includes a manifold housing 122 and an irrigation diverter 128 connected together and extending along the longitudinal axis A1. While shown as separate components, in some examples, the housing 122 and diverter 128 can be formed integrally. Thus, the term “connected” can also, in certain examples, be taken to mean “integral”. When connected, the housing 122 and diverter 128 define an irrigation chamber 144 (FIGS. 7-10), which is discussed in greater detail below.

Figure 7:
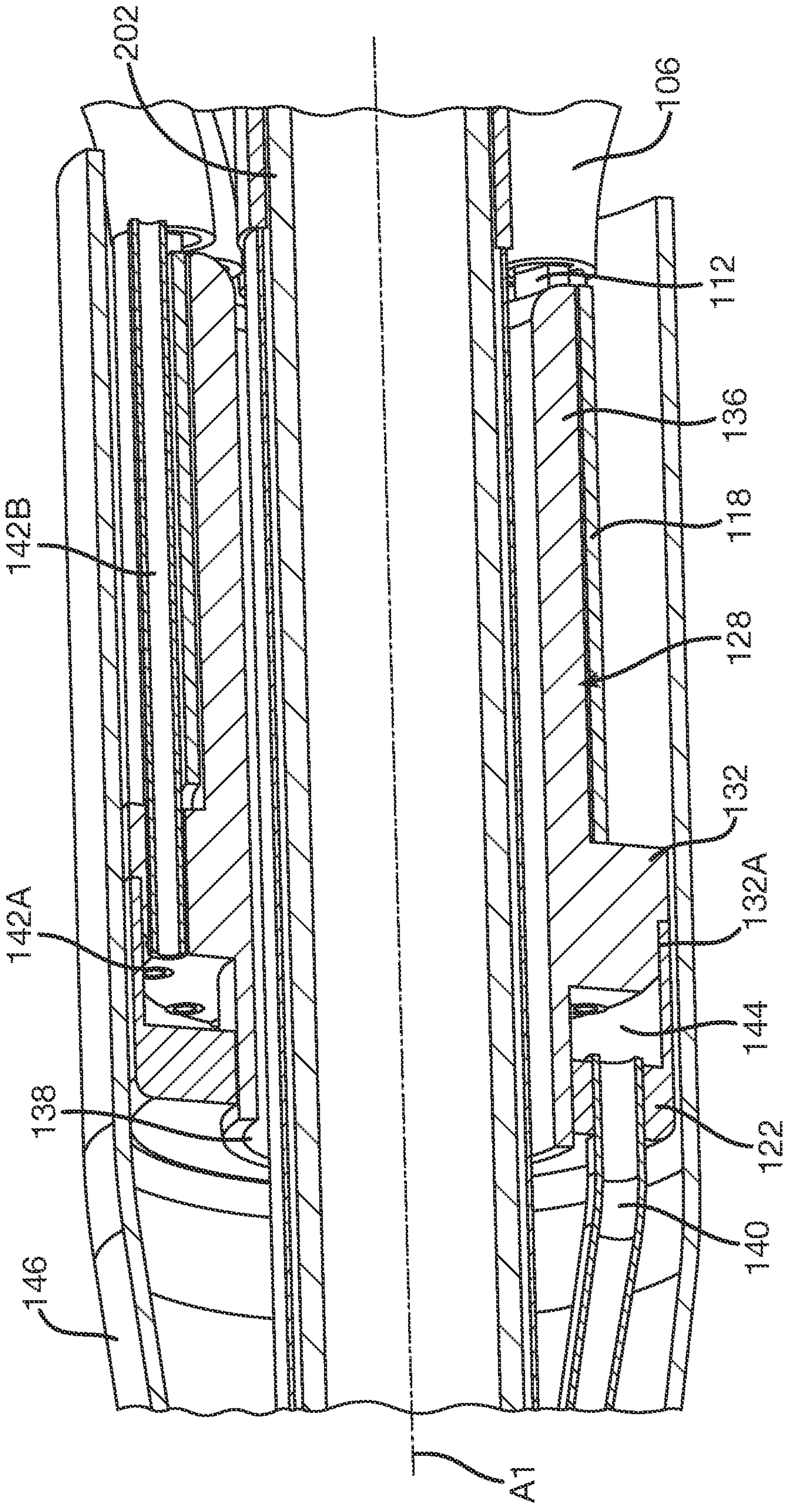
FIG. 7 is a schematic pictorial illustration showing a perspective view of the proximal end of the end effector, shown in cross-section to illustrate certain features, in accordance with the disclosed technology.
Figure 8:
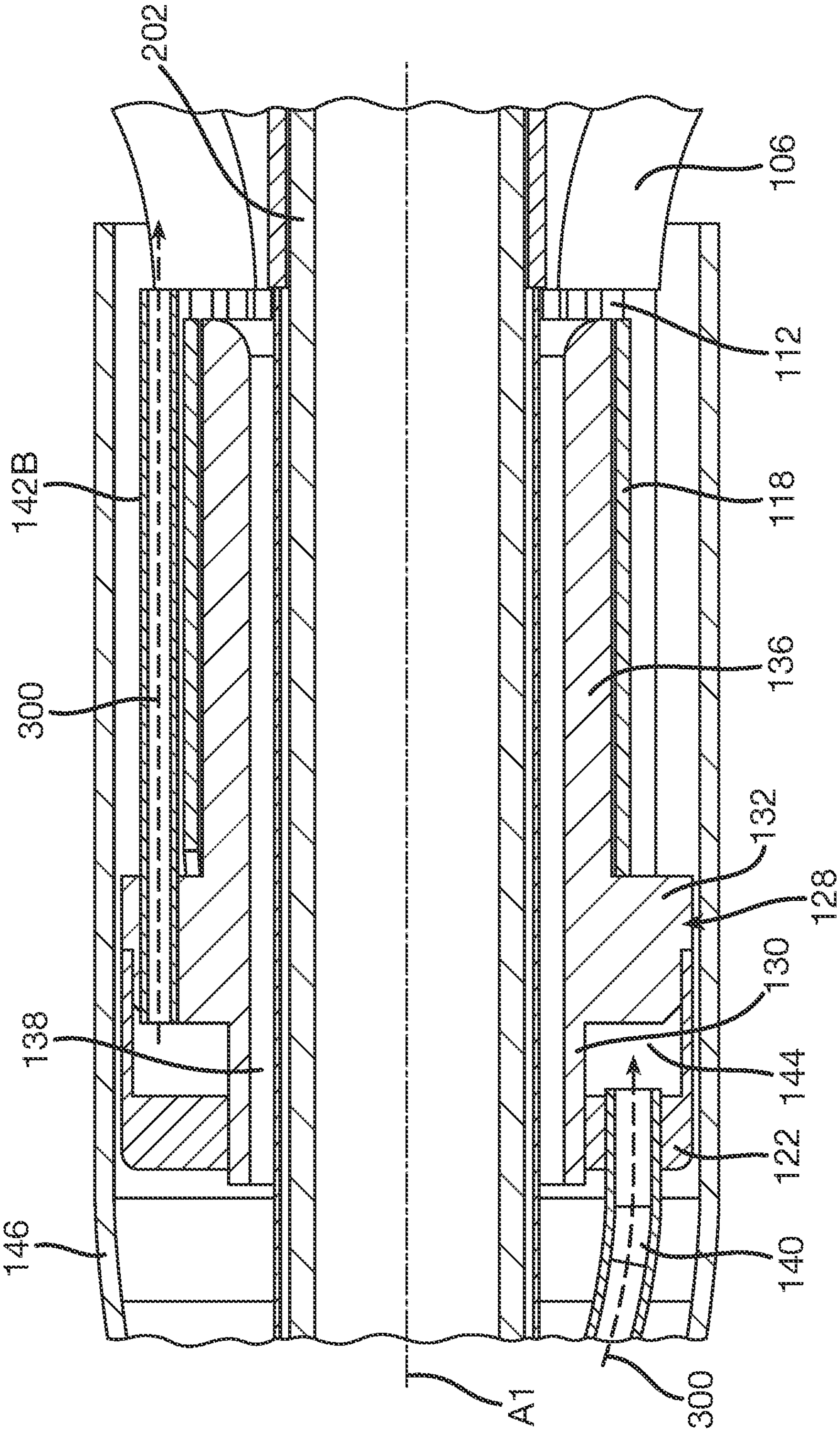
FIG. 8 is a schematic pictorial illustration showing a cross-sectional view of the proximal end of the end effector, cut relative to line 8-8 in FIG. 2, in accordance with the disclosed technology.
Figure 9:
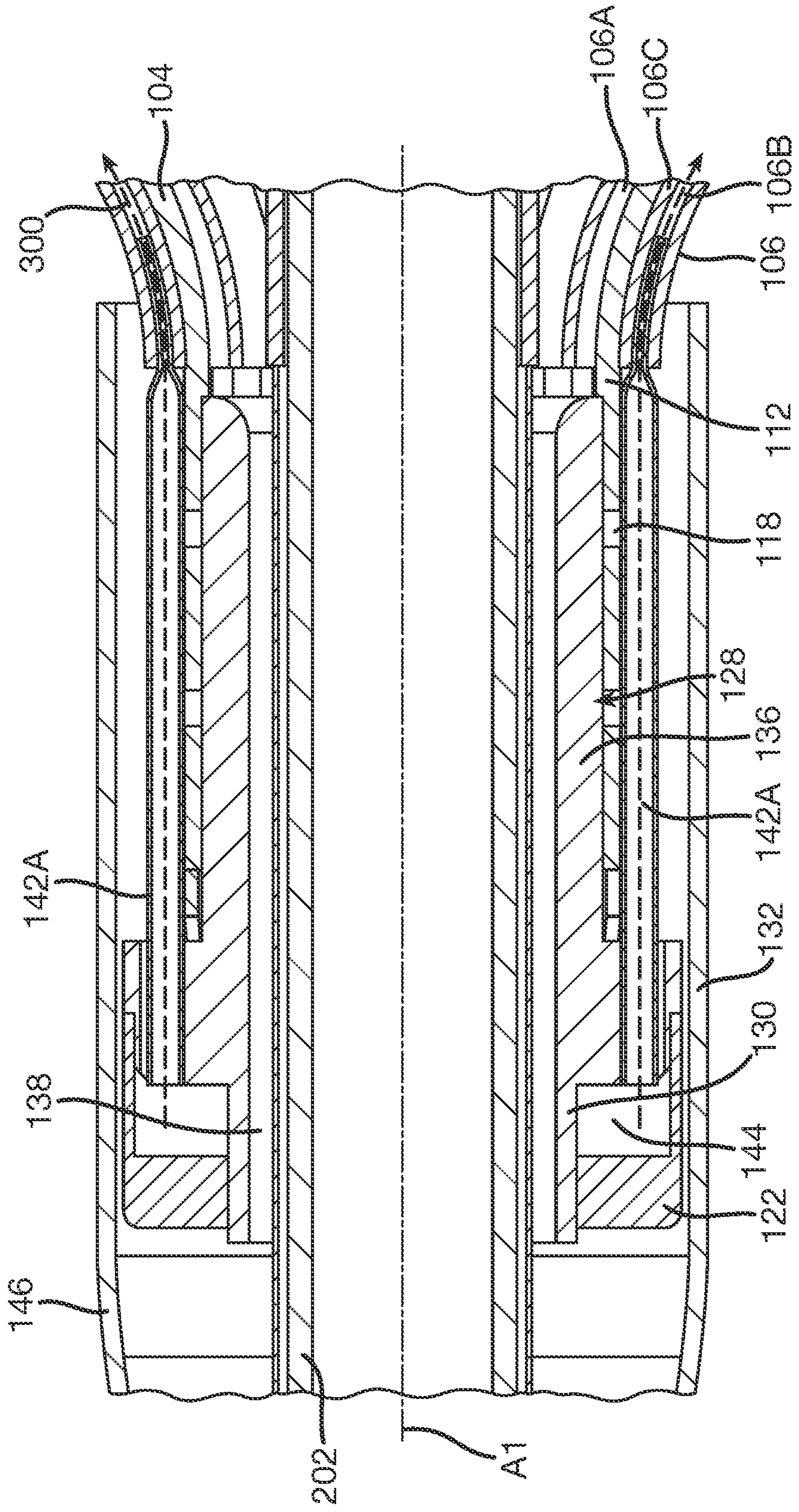
FIG. 9 is a schematic pictorial illustration showing a cross-sectional view of the proximal end of the end effector, cut relative to line 9-9 in FIG. 2, in accordance with the disclosed technology.
Figure 10:
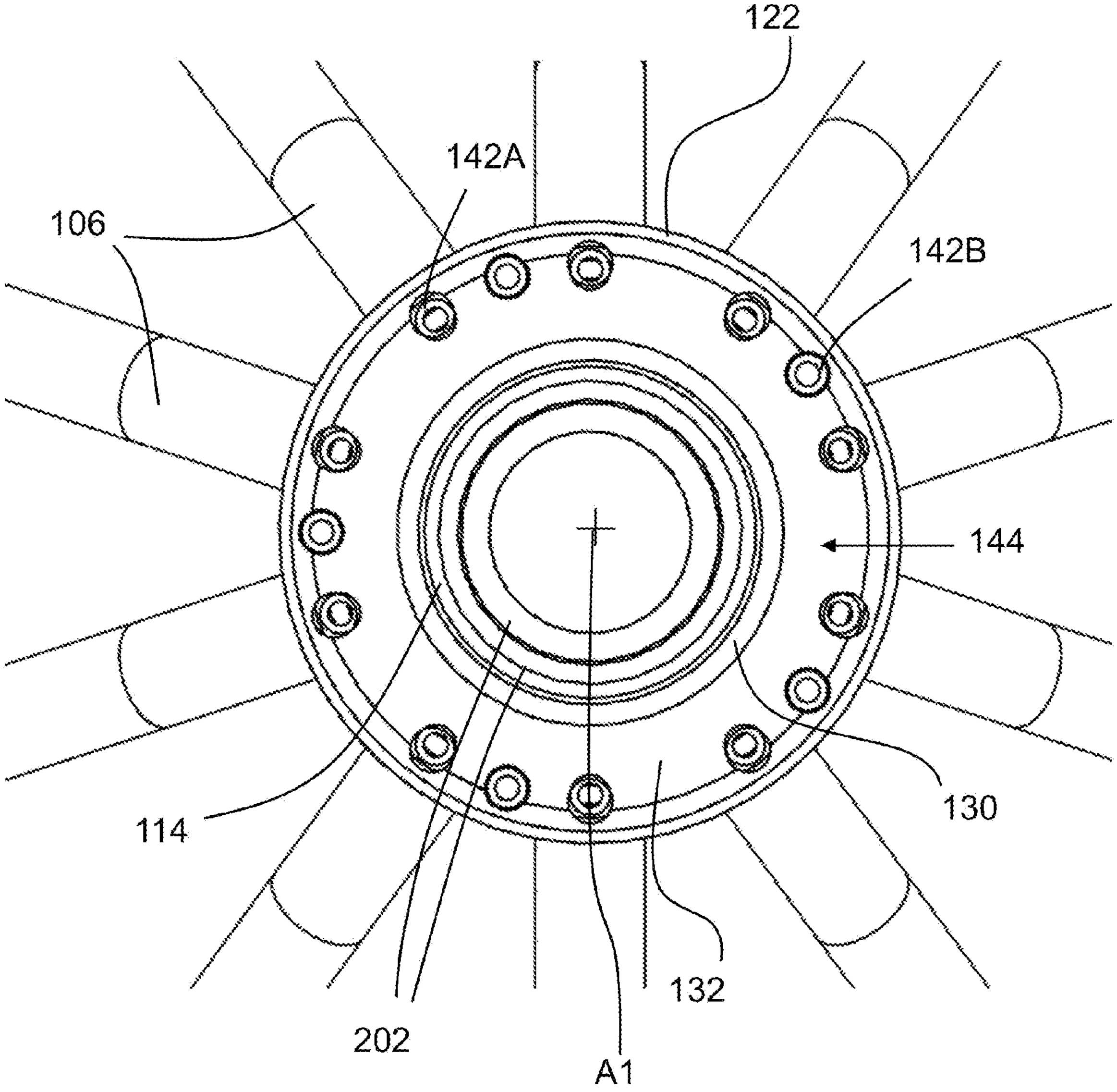
FIG. 10 is a schematic pictorial illustration showing a cross-sectional view of the proximal end of the end effector, cut relative to line 10-10 in FIG. 3, in accordance with the disclosed technology.

FIG. 7 is a schematic pictorial illustration showing a perspective view perspective view of the proximal end of the end effector 100, shown in cross-section to illustrate certain features of the disclosed technology. FIG. 8 is a schematic pictorial illustration showing a cross-sectional view of the proximal end of the end effector 100, cut relative to line 8-8 in FIG. 2. FIG. 9 is a schematic pictorial illustration showing a cross-sectional view of the proximal end of the end effector 100, cut relative to line 9-9 in FIG. 2. FIG. 10 is a schematic pictorial illustration showing a cross-sectional view of the proximal end of the end effector 100, cut relative to line 10-10 in FIG. 3.

Making reference to FIGS. 5-10, the manifold housing 122 is generally cylindrical in form and defines a housing lumen 124 as well as a hollow portion (right side of the housing 122 relative to the orientation shown in FIGS. 8 and 9). The housing lumen 124 is parallel or coaxial with the longitudinal axis A1. Offset axially from the housing lumen is a housing conduit 126 that connects with a main line irrigation tube 140. As seen particularly in FIGS. 6-8, the housing conduit 126 is formed in a proximal wall of the housing 122 that is adjacent the hollow portion.

Further to the above, the irrigation diverter 128 is generally cylindrical in form. The irrigation diverter 128 includes a first diverter shaft 130, a diverter ring 132, and a second diverter shaft 136 that are all axially aligned along the longitudinal axis A1, with a diverter lumen 138 being defined therethrough. The first diverter shaft 130 and second diverter shaft 136 are disposed on opposing sides of the diverter ring 132 along the longitudinal axis A1. As particularly shown in FIGS. 5 and 7-9, the spine coupler 130 encircles the second diverter shaft 136 to connect it thereto.

As shown particularly in FIGS. 7-9, the first diverter shaft 130 nests within the housing lumen 124. The diverter ring 132 has a larger outer diameter than the first diverter shaft 130 and the second diverter shaft 136 and defines one or more diverter conduits 134 radially disposed about and running along the longitudinal axis A1 and spaced about a circumferential periphery of the diverter ring 132. In other words, the diverter conduits 134 are laterally offset from the longitudinal axis A1 and extend parallel thereto.

A lip 132A is also formed in an outer surface of the diverter ring 132. As seen particularly in FIGS. 7-9, the lip nests with an inner annular surface of the manifold housing 122. Accordingly, due to the respective nestings of the first diverter shaft 130 and the diverter ring 132 with the manifold housing 122, the resulting space therebetween forms an irrigation chamber 144 that is annular in form. The irrigation chamber 144 fluidically connects the main line irrigation tube 140 with the diverter conduits, and is discussed in greater detail below. Moreover, due to the axially aligned lumens 124, 138 and annular form of the irrigation chamber 144, the actuator rod 202 is able to pass through the lumens 124, 138 and run at least partially through the elongated shaft 200.

With reference now primarily to FIGS. 5-10, each diverter conduit 134 is connected to a diverter irrigation tube 142. More specifically, a proximal end of each diverter irrigation tube 142 can be inserted into a respective diverter conduit 134 such that the diverter irrigation tube 142 extends away from the irrigation manifold 120 and towards the distal end of the end effector 100. The As seen particularly in FIG. 6, the diverter irrigation tubes 142 are oriented parallel to one another and the longitudinal axis A1. The diverter irrigation tubes 142 are disposed beyond the spine coupler 118 in a radial direction (FIGS. 5 and 7-9). In other words, the diverter irrigation tubes 142 are spaced further away from the longitudinal axis A1 than a distance of the spine coupler 118 to the longitudinal axis (i.e., the radius of the spine coupler 118). With reference to FIG. 5, the diverter irrigation tubes 142 encircle the spine coupler 118 and the second diverter shaft 136.

With continued reference to FIGS. 5-10, the diverter irrigation tubes 142 can be classified into two sub-groups of tubes. Specifically, the diverter irrigation tubes 142 include first diverter irrigation tubes 142A and second diverter irrigation tubes 142B. As seen best in FIG. 5, the diverter conduits 134 are generally grouped into sets of three, and a second diverter irrigation tube 142B is sandwiched between two adjacent first diverter irrigation tubes 142A. Accordingly, in the disclosed example, there is a 2:1 ratio of first diverter irrigation tubes 142A to second diverter irrigation tubes 142B, although other ratios may be employed without departing from the spirit and scope of the present disclosure.

As shown particularly in FIGS. 5 and 9, a distal end of each first diverter irrigation tube 142A is connected with/received by the irrigation conduit 106B of a respective jacket 106. This connection results in a continuous fluid path from the irrigation chamber 144 to the irrigation conduits 106B. As schematically exemplified by the dashed line 300 in FIG. 3. irrigation fluid 300 from the fluid source 302 routes through the main line irrigation tube 140, into the irrigation manifold 120 (specifically, the irrigation chamber 144), through each first diverter irrigation tube 142 (only one path is shown in FIG. 3 for illustrative purposes), into each irrigation conduit 106B, and exiting into the patient 23 through or proximal the electrodes 26 disposed on each spine 104.

In examples described herein, electrodes 26 can be configured to deliver ablation energy (IRE and/or RF) to tissue in heart 12. In addition to using electrodes 26 to deliver ablation energy, the electrodes 26 can also be used to determine the location of the end effector 100 and/or to measure a physiological property such as local surface electrical potentials at respective locations on tissue in heart 12. The electrodes 26 can be biased such that a greater portion of the electrode 26 faces outwardly from the end effector 100 such that the electrodes 26 deliver a greater amount of electrical energy outwardly away from the end effector 100 (i.e., toward the heart 12 tissue) than inwardly toward the end effector 100.

Examples of materials ideally suited for forming electrodes 26 include gold, platinum, and palladium (and their respective alloys). These materials also have high thermal conductivity which allows the minimal heat generated on the tissue (i.e., by the ablation energy delivered to the tissue) to be conducted through the electrodes to the back side of the electrodes (i.e., the portions of the electrodes on the inner sides of the spines), and then to the blood pool in heart 12.

The electrodes 26 may be provided with one or more outlets 26A (FIG. 2) therethrough or immediately proximal thereto. In use, as the irrigation fluid 300 passes through the irrigation conduits 106B, portions of the fluid 300 is allowed to exit through the outlets 26A, such that irrigation is provided directly at each electrode 26. In some examples, some irrigation fluid 300 can continue all the way down the jacket 106 past the most distal electrode 26 and exit proximal the annulus 114 (see FIG. 4 for reference). In other examples, the annulus 114 or another element can be configured to occlude the distal end of the irrigation conduit 106 to block fluid flow or be adjustable to selectively permit fluid flow out of the distal end as needed by the physician 24.

With specific reference now being made to FIGS. 5, 7 and 8, a distal end of each second diverter irrigation tube 142B is not received by an irrigation conduit 106B. Rather, the second diverter irrigation tubes 142B terminate outside the conduits 106B such that irrigation fluid 300 is delivered directly to the patient 23, in use, as opposed to first being routed through a conduit. In the illustrated example, distal ends of the second diverter irrigation tubes 142B terminate near a proximal end of the jackets 106 along the longitudinal axis A1. As depicted in FIG. 8, irrigation fluid 300 that enters the irrigation chamber 144 is, in addition to being routed through the first diverter irrigation tubes 142A, routed through the second diverter irrigation tubes 142B to irrigate near a proximal end of the end effector 100. In some examples, the second diverter irrigation tubes 142B may be omitted.

As illustrated by the foregoing, the irrigation manifold 120 and diverter tubes 142, along with the irrigation conduits 106B formed in the jackets 106, enable even distribution of irrigation around the electrodes 26 while simultaneously providing a way to provide irrigation directly within a patient 23. As will be appreciated, the presently disclosed technology can be modified in various ways without departing from the spirit and scope of the present disclosure.

The disclosed technology described herein can be further understood according to the following clauses:

Clause 1. An irrigation manifold for a medical device, the irrigation manifold comprising: a housing extending along a longitudinal axis defining a housing lumen and a housing conduit offset from the housing lumen, the housing conduit being configured to connect with a main line irrigation tube; and a diverter defining a diverter lumen connecting with the housing to define an irrigation chamber, and comprising: a first shaft nesting within the housing lumen; a diverter ring defining a plurality of diverter conduits disposed radially about the longitudinal axis and connecting with a distal end of the housing, each diverter conduit being configured to connect with a diverter irrigation tube that routes a fluid to an end effector of the medical device.

Clause 2. The irrigation manifold of clause 1, the irrigation chamber being annular in form.

Clause 3. The irrigation manifold of any one of clauses 1-2, the diverter ring defining a lip that nests with an inner annular surface of the housing.

Clause 4. The irrigation manifold of any one of clauses 1-3, the plurality of diverter conduits being spaced about a circumferential periphery of the diverter ring.

Clause 5. The irrigation manifold of any one of clauses 1-4, the diverter further comprising a second shaft, the first shaft and the second shaft being disposed on opposing sides of the diverter ring.

Clause 6. An irrigation system for a medical device, the irrigation system comprising: an irrigation manifold comprising: a housing defining a housing conduit and extending along a longitudinal axis; and a diverter connecting with the housing to define an annular irrigation chamber and defining a plurality of diverter conduits; a main line irrigation tube connected to the housing conduit and configured to connect with a fluid source; and a plurality of diverter irrigation tubes, each connected to a respective diverter conduit, the plurality of diverter irrigation tubes being configured to route a fluid to an end effector of the medical device.

Clause 7. The irrigation system of clause 6, further comprising the end effector, the end effector comprising a plurality of spines disposed about the longitudinal axis, each spine comprising a proximal end connected to the irrigation manifold.

Clause 8. The irrigation system of clause 7, the end effector further comprising a plurality of jackets, each jacket defining: a spine channel receiving a respective spine of the plurality of spines; and an irrigation conduit that receives a respective diverter irrigation tube of the plurality of the plurality of diverter irrigation tubes.

Clause 9. The irrigation system of clause 8, the plurality of diverter irrigation tubes comprising first diverter irrigation tubes and second diverter irrigation tubes, each first diverter irrigation tube being received by the irrigation conduit of a respective jacket of the plurality of jackets, and each second diverter irrigation tube comprising a distal end disposed outside the plurality of jackets.

Clause 10. The irrigation system of clause 9, each second diverter irrigation tube being sandwiched by adjacent first diverter irrigation tubes.

Clause 11. The irrigation system of any one of clauses 8-10, each spine channel and each irrigation conduit spanning an entire length of each jacket.

Clause 12. The irrigation system of clause 11, further comprising an annulus connected to a distal end of the plurality of spines, the annulus occluding a distal end of each irrigation conduit.

Clause 13. The irrigation system of clause 11, further comprising an annulus connected to a distal end of the plurality of spines, the annulus being configured to permit the fluid to exit a distal end of each irrigation conduit.

Clause 14. The irrigation system of any one of clauses 7-13, further comprising at least one electrode connected to each spine, at least a portion of the plurality of diverter irrigation tubes being configured to route the fluid through at least one outlet defined in or proximal the at least one electrode.

Clause 15. The irrigation system of any one of clauses 9-11, further comprising at least one electrode connected to each jacket, each first diverter irrigation tube being configured to route the fluid through respective irrigation conduits of the jackets to the at least one electrode.

Clause 16. The irrigation system of clause 15, further comprising an outlet defined in or disposed proximal each electrode of the at least one electrode.

Clause 17. An end effector for a medical device, the end effector comprising: an irrigation manifold extending along a longitudinal axis and comprising: a housing defining a housing lumen and a housing conduit; and a diverter defining a diverter lumen, connecting with the housing to define an irrigation chamber, and defining at least one diverter conduit, with fluid being configured to flow into the irrigation chamber via the housing conduit and out of the irrigation chamber via the at least one diverter conduit; at least one spine connected to the irrigation manifold at a proximal end of the at least one spine and configured to bow radially outward from the longitudinal axis and to move between an expanded configuration and a collapsed configuration, the at least one diverter conduit being configured to route the fluid along the at least one spine; an actuator rod passing through the housing lumen and the diverter lumen and connected to a distal end of the at least one spine, the actuator rod being configured to move the at least one spine between the expanded configuration and the collapsed configuration.

Clause 18. The end effector of clause 17, the at least one spine being integrally formed from a tube stock.

Clause 19. The end effector of any one of clauses 17-18, further comprising a distal hub integral with the at least one spine, the actuator rod being connected to the distal hub.

Clause 20. The end effector of any one of clauses 17-19, further comprising a spine coupler that is shaped to couple the proximal end of the at least one spine to the diverter.

Clause 21. The end effector of clause 20, the spine coupler encircling at least a portion of the diverter.

Clause 22. The end effector of any one of clauses 20-21, further comprising at least one diverter irrigation tube that is connected to the at least one diverter conduit and is disposed beyond the spine coupler in a radial direction.

Clause 23. The end effector of any one of clauses 17-22, further comprising at least one electrode connected to the at least one spine, the at least one electrode comprising an outlet configured to permit the fluid to exit therethrough.

Clause 24. The end effector of any one of clauses 17-23 further comprising at least one jacket, the at least one jacket defining: a spine channel receiving the at least one spine; and an irrigation conduit that connects with the at least one diverter conduit.

Clause 25. The end effector of clause 24, the at least one jacket comprising a wall separating the spine channel and the irrigation conduit.

Clause 26. The end effector of any one of clauses 17-25, the actuator rod defining an actuator rod lumen coaxial with the longitudinal axis.

Clause 27. The end effector of any one of clauses 17-26, the actuator rod being configured to translate along the longitudinal axis configured to move the at least one spine between the expanded configuration and the collapsed configuration.

Clause 28. The end effector of any one of clauses 17-27, the housing conduit and the at least one diverter conduit being laterally offset from the longitudinal axis and extending parallel to the longitudinal axis.

The examples described above are cited by way of example, and the disclosed technology is not limited by what has been particularly shown and described hereinabove. Rather, the scope of the disclosed technology includes both combinations and sub combinations of the various features described hereinabove, as well as variations and modifications thereof which would occur to persons skilled in the art upon reading the foregoing description and which are not disclosed in the prior art.

What is claimed is:

1. An irrigation system for a medical device, the irrigation system comprising:

an irrigation manifold comprising:

a housing defining a housing conduit and extending along a longitudinal axis; and a diverter connecting with the housing to define an annular irrigation chamber and defining a plurality of diverter conduits;

a main line irrigation tube connected to the housing conduit and configured to connect with a fluid source;

a plurality of diverter irrigation tubes, each connected to a respective diverter conduit, the plurality of diverter irrigation tubes being configured to route a fluid to an end effector of the medical device; and further comprising the end effector, the end effector comprising a plurality of spines disposed about the longitudinal axis, each spine comprising a proximal end connected to the irrigation manifold, the end effector further comprising a plurality of jackets, each jacket defining:

a spine channel receiving a respective spine of the plurality of spines; and an irrigation conduit that receives a respective diverter irrigation tube of the plurality of diverter irrigation tubes, the plurality of diverter irrigation tubes comprising first diverter irrigation tubes and second diverter irrigation tubes, each first diverter irrigation tube being received by the irrigation conduit of a respective jacket of the plurality of jackets, and each second diverter irrigation tube comprising a distal end disposed outside the plurality of jackets.

2. The irrigation system of claim 1, each second diverter irrigation tube being sandwiched by adjacent first diverter irrigation tubes.

3. The irrigation system of claim 1, each spine channel and each irrigation conduit spanning an entire length of each jacket.

4. The irrigation system of claim 3, further comprising an annulus connected to a distal end of the plurality of spines, the annulus occluding a distal end of each irrigation conduit.

5. The irrigation system of claim 1, further comprising at least one electrode connected to each spine, at least a portion of the plurality of diverter irrigation tubes being configured to route the fluid through at least one outlet defined in or proximal the at least one electrode.

6. The irrigation system of claim 1, further comprising at least one electrode connected to each jacket, each first diverter irrigation tube being configured to route the fluid through respective irrigation conduits of the jackets to the at least one electrode.

7. The irrigation system of claim 6, further comprising an outlet defined in or disposed proximal each electrode of the at least one electrode.

8. An end effector for a medical device, the end effector comprising:

an irrigation manifold extending along a longitudinal axis and comprising:

a housing defining a housing lumen and a housing conduit; and a diverter defining a diverter lumen, connecting with the housing to define an irrigation chamber, and defining at least one diverter conduit, with fluid being configured to flow into the irrigation chamber via the housing conduit and out of the irrigation chamber via the at least one diverter conduit;

a plurality of spines connected to the irrigation manifold at a proximal end of the at least one spine and configured to bow radially outward from the longitudinal axis and to move between an expanded configuration and a collapsed configuration, the at least one diverter conduit being configured to route the fluid along the plurality of spines;

an actuator rod passing through the housing lumen and the diverter lumen and connected to a distal end of the plurality of spines, the actuator rod being configured to move the plurality of spines between the expanded configuration and the collapsed configuration;

each spine of the plurality of spines comprising a proximal end connected to the irrigation manifold; and a plurality of jackets, each jacket defining:

a spine channel receiving a respective spine of the plurality of spines; and an irrigation conduit that receives a respective diverter irrigation tube of a plurality of diverter irrigation tubes, the plurality of diverter irrigation tubes comprising first diverter irrigation tubes and second diverter irrigation tubes, each first diverter irrigation tube being received by the irrigation conduit of a respective jacket of the plurality of jackets, and each second diverter irrigation tube comprising a distal end disposed outside the plurality of jackets.

9. The end effector of claim 8, further comprising at least one electrode connected to the plurality of spines, the at least one electrode comprising an outlet configured to permit the fluid to exit therethrough.

10. The end effector of claim 8, each jacket of the plurality of jackets comprising a wall separating the spine channel and the irrigation conduit.

11. The end effector of claim 8, the housing conduit and the at least one diverter conduit being laterally offset from the longitudinal axis and extending parallel to the longitudinal axis.

12. An irrigation system for a medical device, the irrigation system comprising:

an irrigation manifold comprising:

a housing defining a housing conduit and extending along a longitudinal axis; and a diverter connecting with the housing to define an annular irrigation chamber and defining a plurality of diverter conduits;

a main line irrigation tube connected to the housing conduit and configured to connect with a fluid source;

a plurality of diverter irrigation tubes, each connected to a respective diverter conduit, the plurality of diverter irrigation tubes being configured to route a fluid to an end effector of the medical device; and the end effector comprising a plurality of spines disposed about the longitudinal axis, each spine comprising a proximal end connected to the irrigation manifold, the end effector further comprising a plurality of jackets, each jacket defining:

a spine channel receiving a respective spine of the plurality of spines; and an irrigation conduit that receives a respective diverter irrigation tube of the plurality of diverter irrigation tubes, each spine channel and each irrigation conduit spanning an entire length of each jacket.

13. The irrigation system of claim 12, further comprising an annulus connected to a distal end of the plurality of spines, the annulus occluding a distal end of each irrigation conduit.

14. The irrigation system of claim 13, further comprising at least one electrode connected to each spine of the plurality of spines, at least a portion of the plurality of diverter irrigation tubes being configured to route the fluid through at least one outlet defined in or proximal the at least one electrode.

15. The irrigation system of claim 13, further comprising at least one electrode connected to each jacket of the plurality of jackets, each first diverter irrigation tube being configured to route the fluid through respective irrigation conduits of the plurality of jackets to the at least one electrode.

16. The irrigation system of claim 15, further comprising an outlet defined in or disposed proximal each electrode of the at least one electrode.

* * * * *